US008158437B2

(12) United States Patent
Swager et al.

(10) Patent No.: US 8,158,437 B2
(45) Date of Patent: Apr. 17, 2012

(54) LUMINESCENT DETECTION OF HYDRAZINE AND HYDRAZINE DERIVATIVES

(75) Inventors: Timothy M. Swager, Newton, MA (US); Samuel W. Thomas, III, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 43 days.

(21) Appl. No.: 12/308,298

(22) PCT Filed: Aug. 2, 2007

(86) PCT No.: PCT/US2007/017380
§ 371 (c)(1),
(2), (4) Date: Dec. 7, 2009

(87) PCT Pub. No.: WO2008/019086
PCT Pub. Date: Feb. 14, 2008

(65) Prior Publication Data
US 2010/0112715 A1    May 6, 2010

Related U.S. Application Data

(60) Provisional application No. 60/835,828, filed on Aug. 4, 2006.

(51) Int. Cl.
*G01N 21/64* (2006.01)
*G01N 33/00* (2006.01)
(52) U.S. Cl. ........ 436/111; 436/106; 436/112; 436/113; 436/172
(58) Field of Classification Search .................. 436/106, 436/111–113, 172
See application file for complete search history.

(56) References Cited

U.S. PATENT DOCUMENTS

| | | | |
|---|---|---|---|
| 4,356,429 A | 10/1982 | Tang | |
| 4,513,078 A * | 4/1985 | Sandrik et al. | 430/496 |
| 4,687,732 A | 8/1987 | Ward et al. | |
| 4,927,768 A | 5/1990 | Coughlin et al. | |
| 4,946,890 A | 8/1990 | Meador | |
| 4,992,302 A | 2/1991 | Lindmayer | |
| 5,155,149 A | 10/1992 | Atwater et al. | |
| 5,157,261 A | 10/1992 | Gret et al. | |
| 5,194,393 A | 3/1993 | Hugl et al. | |

(Continued)

FOREIGN PATENT DOCUMENTS

DE     197 44 792 A1    4/1999
(Continued)

OTHER PUBLICATIONS

Ellis, D. L. et al, Analytical Chemistry 1996, 68, 817-822.*
(Continued)

*Primary Examiner* — Arlen Soderquist
(74) *Attorney, Agent, or Firm* — Wolf, Greenfield & Sacks, P.C.

(57) ABSTRACT

The present invention generally relates to methods for modulating the optical properties of a luminescent polymer via interaction with a species (e.g., an analyte). In some cases, the present invention provides methods for determination of an analyte by monitoring a change in an optical signal of a luminescent polymer upon exposure to an analyte. Methods of the present invention may be useful for the vapor phase detection of analytes such as explosives and toxins. The present invention also provides methods for increasing the luminescence intensity of a polymer, such as a polymer that has been photobleached, by exposing the luminescent polymer to a species such as a reducing agent.

41 Claims, 10 Drawing Sheets

U.S. PATENT DOCUMENTS

| | | | |
|---|---|---|---|
| 5,236,808 A | 8/1993 | Smothers | |
| 5,244,813 A | 9/1993 | Walt et al. | |
| 5,254,633 A | 10/1993 | Han et al. | |
| 5,364,797 A | 11/1994 | Olson et al. | |
| 5,414,069 A | 5/1995 | Cumming et al. | |
| 5,451,683 A | 9/1995 | Barrett et al. | |
| 5,511,547 A | 4/1996 | Markle et al. | |
| 5,512,490 A | 4/1996 | Walt et al. | |
| 5,532,129 A | 7/1996 | Heller | |
| 5,540,999 A | 7/1996 | Yamamoto et al. | |
| 5,546,889 A | 8/1996 | Wakita et al. | |
| 5,554,747 A | 9/1996 | Sharma et al. | |
| 5,556,524 A | 9/1996 | Albers | |
| 5,563,056 A | 10/1996 | Swan et al. | |
| 5,565,322 A | 10/1996 | Heller | |
| 5,580,527 A | 12/1996 | Bell et al. | |
| 5,585,646 A | 12/1996 | Kossovsky et al. | |
| 5,591,787 A | 1/1997 | Schlennert et al. | |
| 5,597,890 A | 1/1997 | Jenekhe | |
| 5,607,864 A | 3/1997 | Ricchiero et al. | |
| 5,629,353 A | 5/1997 | Steckle, Jr. et al. | |
| 5,674,751 A * | 10/1997 | Jaduszliwer et al. | 436/116 |
| 5,679,773 A | 10/1997 | Holmes | |
| 5,700,696 A | 12/1997 | Chandross et al. | |
| 5,705,348 A | 1/1998 | Meade et al. | |
| 5,709,994 A | 1/1998 | Pease et al. | |
| 5,710,187 A | 1/1998 | Steckle, Jr. et al. | |
| 5,710,197 A | 1/1998 | Fischer et al. | |
| 5,723,218 A | 3/1998 | Haugland et al. | |
| 5,869,592 A | 2/1999 | Gagné et al. | |
| 5,925,517 A | 7/1999 | Tyagi et al. | |
| 6,020,426 A | 2/2000 | Yamaguchi et al. | |
| 6,259,277 B1 | 7/2001 | Tour et al. | |
| 6,328,932 B1 * | 12/2001 | Carter et al. | 422/82.06 |
| 6,509,110 B1 | 1/2003 | Salbeck et al. | |
| 6,556,335 B2 | 4/2003 | Jones et al. | |
| 6,589,731 B1 | 7/2003 | Chen et al. | |
| 6,605,693 B1 | 8/2003 | Becker et al. | |
| 6,713,298 B2 | 3/2004 | McDevitt et al. | |
| 6,743,640 B2 | 6/2004 | Whitten et al. | |
| 6,783,814 B2 | 8/2004 | Swager et al. | |
| 6,962,757 B2 | 11/2005 | Epstein et al. | |
| 7,186,355 B2 | 3/2007 | Swager et al. | |
| 7,208,122 B2 | 4/2007 | Swager et al. | |
| 7,393,503 B2 | 7/2008 | Swager et al. | |
| 7,417,146 B2 | 8/2008 | Huo | |
| 2002/0177136 A1 | 11/2002 | McBranch et al. | |
| 2003/0054413 A1 | 3/2003 | Kumaraswamy et al. | |
| 2003/0134959 A1 | 7/2003 | Hancock et al. | |
| 2003/0178607 A1* | 9/2003 | Swager et al. | 252/582 |
| 2004/0121337 A1 | 6/2004 | Deans et al. | |
| 2004/0175768 A1 | 9/2004 | Kushon et al. | |
| 2004/0235184 A1 | 11/2004 | Swager | |
| 2004/0241768 A1 | 12/2004 | Whitten et al. | |
| 2005/0014160 A1 | 1/2005 | Kumaraswamy et al. | |
| 2005/0157261 A1 | 7/2005 | Hanebuchi et al. | |
| 2005/0226775 A1 | 10/2005 | Aker et al. | |
| 2006/0024707 A1 | 2/2006 | Deans et al. | |
| 2006/0120917 A1 | 6/2006 | Swager et al. | |

FOREIGN PATENT DOCUMENTS

| | | |
|---|---|---|
| DE | 198 06 037 A1 | 9/1999 |
| EP | 0 442 123 A1 | 8/1991 |
| EP | 0581058 A1 | 2/1994 |
| EP | 1 011 154 A1 | 6/2000 |
| JP | 06-322078 | 11/1994 |
| WO | WO 89/00593 | 1/1989 |
| WO | WO 95/16681 | 6/1995 |
| WO | WO 99/19419 A1 | 4/1999 |
| WO | WO 99/57222 | 11/1999 |
| WO | WO 00/53655 A1 | 9/2000 |
| WO | WO 01/57140 A1 | 8/2001 |
| WO | WO 02/16463 A2 | 2/2002 |
| WO | WO 03/048226 A2 | 6/2003 |
| WO | WO 2004/057014 A2 | 7/2004 |

OTHER PUBLICATIONS

Moroni, M. et al, Macromolecules 1997, 30, 1964-1972.*
Yuan J. et al, SPIE 2001, 4205, 170-179.*
Pei, J. et al, Macromolecules 2003, 36, 323-327.*
Arias-Marin, E. et al, Macromolecules 2003, 36, 3570-3579.*
Tsai, F.-C. et al, Macromolecules 2005, 38, 1958-1966.*
Zhou, G. et al, Macromolecules 2005, 38, 2148-2153.*
Brown, A. B. et al, Sensors and Actuators B 2005, 110, 8-12.*
Dudek, S. P. et al, Journal of the American Chemical Society 2005, 127, 11763-11768.*
Pei, Q. et al, Journal of the American Chemical Society 1996, 118, 3922-3929.*
Ng, S. C. et al, Synthetic Metals 1999, 100, 269-277.*
Abraham et al., "Hydrogen bonding. Part 29. Characterization of 14 Sorbent Coatings for Chemical Microsensors using a New Solvation Equation," J. Chem. Soc. Perkin Trans. 1995, 2, 369-378.
Achyuthan et al., "Fluorescence Superquenching of Conjugated Polyelectrolytes: Applications for Biosensing and Drug Discovery," J. Mat. Chem. 2005, 15, 2648.
Amara et al., "Synthesis and Properties of Poly(phenylene ethynylene)s with Pendant Hexafluoro-2-propanol Groups," Macromolecules 2005, 38, 9091-9094.
Bergstedt et al., "Superquenching of Fluorescent Polyelectrolytes and its Applications for Chemical and Biological Sensing," Proc. SPIE 2001, 4279, 94.
Brabec et al., "Plastic Solar Cells," Adv. Funct. Mater. 2001, 11(1), 15.
Chen et al., "Surfactant-induced Modification of Quenching of Conjugated Polymer Fluorescence by Electron Acceptors: Applications for Chemical Sensing," Chem. Phys. Lett. 2000, 27, 330.
Chen et al., "Highly sensitive biological and chemical sensors based on reversible fluorescence quenching in a conjugated polymer," PNAS 1999, 96(22), 12287.
Chen et al., "Tuning the Properties of Conjugated Polyelectrolytes through Surfactant Complexation," J. Am. Chem. Soc. 2000, 122, 9302-9303.
Cotts et al., "Equilibrium Flexibility of a Rigid Linear Conjugated Polymer," Macromolecules 1996, 29, 7323.
Dagani, "A Better Sensor for Nerve Gas," C&E News, Mar. 10, 2003, 12.
Deans et al., "A Poly(ρ-phenyleneethynylene) with a Highly Emissive Aggregated Phase," J. Am. Chem. Soc. 2000, 122, 8565.
Deng et al., "Direct Observation of the "Pac-Man" Effect from Dibenzofuran-Bridged Cofacial Bisporphyrins," J. Am. Chem. Soc. 2000, 122, 410-411.
Fan et al., "High-Efficiency Fluorescence Quenching of Conjugated Polymers by Proteins," J. Am. Chem. Soc. 2002, 124, 5642.
Fan et al., "Photoluminescence Quenching of Water-Soluble, Conjugated Polymers by Viologen Derivatives: Effect of Hydrophobicity," Langmuir 2003, 19, 3554. Published on Web, Mar. 19, 2003.
Fan et al., "Beyond Superquenching: Hyper-Efficient Energy Transfer from Conjugated Polymers to Gold Nanoparticles," PNAS 2003, 100(11), 6297.
Fiesel et al., "On the Solid State Aggregation of Chiral Substituted Poly(para-phenylene)s (PPPs)," Synthetic Metals 1999, 102, 1457.
Fiesel et al., "Aggregation-induced CD effects in chiral poly(2,5-dialkoxy-1,4-phenylene)s," Acta Polym. 1998, 49, 445.
Fiesel et al., "A chiral poly(para-phenyleneethynylene) (PPE) derivative," Macromol. Rapid Commun. 1998, 19(8), 427.
Fu et al., "Alternating Poly(PyridylVinylenePhenyleneVinylene)s: Synthesis and Solid State Organizations," Tetrahedron 1997, 53(45), 15487.
Gaylord et al., "DNA Hybridization Detection with Water-Soluble Conjugated Polymers and Chromophore-Labeled Single-Stranded DNA," J. Am. Chem. Soc. 2003, 125, 896.
Gaylord et al., "SNP Detection Using Peptide Nucleic Acid Probes and Conjugated Polymers: Applications in Neurodegenerative Disease Identification," PNAS 2005, 102(1), 34.
Gaylord et al., "DNA detection using water-soluble conjugated polymers and peptide nucleic acid probes," PNAS 2002, 99(17), 10954.

Gaylord et al., "Water-Soluble Conjugated Oligomers: Effect of Chain Length and Aggregation on Photoluminescence-Quenching Efficiencies," J. Am. Chem. Soc. 2001, 123(26), 6418.

Goldfinger et al., "Fused Polycyclic Aromatics via Electrophile-Induced Cyclization Reactions: Application to the Synthesis of Graphite Ribbons," J. Am. Chem. Soc. 1994, 116, 7895.

Grate, "Acoustic Wave Microsensor Arrays for Vapor Sensing," Chem Rev. 2000, 100, 2627-2648.

Grate et al., "Hydrogen Bond Acidic Polymers for Surface Acoustic Wave Vapor Sensors and Arrays," Anal. Chem. 1999, 71, 1033-1040.

Halkyard et al., "Evidence of Aggregate Formation for 2,5-Dialkylpoly (ρ-phenyleneethynylenes) in Solution and Thin Films," Macromolecules 1998, 31(25), 8655.

Harrison et al., "Amplified Fluorescence Quenching in a Poly(ρ-phenylene)-Based Cationic Polyelectrolyte," J. Am. Chem. Soc. 2001, 122(35), 8561.

Heeger et al., "Making sense of polymer-based biosensors," PNAS 1999, 96(22), 12219.

Herbich et al. "Fluorescence Quenching by Pyridine and Derivatives Induced by Intermolecular Hydrogen Bonding to Pyrrole-Containing Heteroaromatics," J. Phys. Chem. A. 2002, 106, 2158-2163.

Hoffmeister et al., "Triptycene Polymers," J. Polymer Science 1969, 7, 55-72.

Höger et al., "Synthesis, Aggregation, and Adsorption Phenomena of Shape-Persistent Macrocycles with Extraannular Polyalkyl Substituents," J. Am. Chem. Soc. 2001, 123(24), 5651.

Jones et al., "Building highly sensitive dye assemblies for biosensing from molecular building blocks," PNAS 2001, 98(26), 14769.

Jones et al., "Superquenching and Its Applications in J-Aggregated Cyanine Polymers," Langmuir 2001, 17, 2568.

Jones et al., "Tuning of Superquenching in Layered and Mixed Fluorescent Polyelectrolytes," J. Am. Chem. Soc. 2001, 123, 6726.

Kim et al., "Nanoscale Fibrils and Grids: Aggregated Structures from Rigid-Rod Conjugated Polymers," Macromolecules 1999, 32(5), 1500.

Kim et al. et al., "Ion-Specific Aggregation in Conjugated Polymers: Highly Sensitive and Selective Fluorescent Ion Chemosensors," Angew. Chem. Int. Ed. 2000, 39(21), 3868.

Kim et al., "Control of conformational and interpolymer effects in conjugated polymers," Nature 2001, 411, 1030.

Kim et al., "Directing Energy Transfer within Conjugated Polymer Thin Films," J. Am. Chem. Soc. 2001, 123(46), 11488.

Kim et al., "Structural Control in Thin Layers of Poly)ρ-phenyleneethynylene)s: Photophysical Studies of Langmuir and Langmuir-Blodgett Films," J. Am. Chem. Soc. 2002, 124(26), 7710.

Kim et al., "Ultrafast Energy-Transfer Dynamics between Block Copolymer and π-Conjugated Polymer Chains in Blended Polymeric Systems," Chem. Mater. 2001, 13(8), 2666.

Köhler et al., "Novel Chiral Macrocycles Containing Two Electronically Interacting Arylene Chromophores," Chem. Eur. J., 2001, 7(14), 3000.

Kraft et al., "Electroluminescent Conjugated Polymers—Seeing Polymers in a New Light," Angew. Chem. Int. Ed. 1998, 37, 403.

Kumaraswamy et al., "Fluorescent-Conjugated Polymer Superquenching Facilitates Highly Sensitive Detection of Proteases," PNAS 2004, 101(24), 7511.

Kushon et al., "Detection of DNA Hybridization via Fluorescent Polymer Superquenching," Langmuir 2002, 18(20), 7245.

Kushon et al., "Detection of Single Nucleotide Mismatches via Fluorescent Polymer Superquenching," Langmuir 2003, 19, 6456.

Langveld et al., "Circular Dichroism and Circular Polarization of Photoluminescence of Highly Ordered Poly{3,4-di[(S)-2-methylbutoxy]thiophene}," J. Am. Chem. Soc. 1996, 118(20), 4908.

Levitsky et al., "Energy Migration in a Poly(phenylene ethynylene): Determination of Interpolymer Transport in Anisotropic Langmuir-Blodgett Films," J. Am. Chem. Soc. 1999, 121(7), 1466.

Levitsky et al., "Mass and Energy Transport in Conjugated Polymer Langmuir-Blodgett Films; Conductivity, Fluorescence, and UV-Vis Studies," Macromolecules 2001, 34(7), 2315.

Levitsky, et al., "Rational Design of a Nile Red/Polymer Composite Film for Fluorescence Sensing of Organophosphonate Vapors Using Hydrogen Bond Acidic Polymers," Anal. Chem. 2001, 73, 3441-3448.

Levitsky, et al., "Signal Amplification in Multichromophore Luminescence-Based Sensors," J. Phys. Chem. B, 2001, 105, 8468-8473.

Li et al., "Novel Surfactant-Free Stable Colloidal Nanoparticles Made of Randomly Carboxylated Polystyrene Ionomers," Macromolecules 1997, 30(7), 2201.

Liu et al., "Homogeneous Fluorescence-Based DNA Detection with Water-Soluble Conjugated Polymers," Chem Mater. 2004, 16, 4467.

Liu et al., "Optimization of the Molecular Orbital Energies of Conjugated Polymers for Optical Amplification of Fluorescent Sensors," J. Am. Chem. Soc. 2006, 128, 1188.

Liu et al., "Methods for Strand-Specific DNA Detection with Cationic Conjugated Polymers Suitable for Incorporation into DNA Chips and Microarray," PNAS 2005, 102(3), 589.

Lu et al., "Superquenching in Cyanine Pendant Poly($_L$-lysine) Dyes: Dependence on Molecular Weight, Solvent, and Aggregation," J. Am. Chem. Soc. 2002, 124(3), 483.

Lu et al., "Surface-Enhanced Superquenching of Cyanine Dyes as J-Aggregates on Laponite Clay Nanoparticles," Langmuir 2002, 18, 7706.

Lu et al., "Biocidal Activity of a Light-Absorbing Fluorescent Conjugated Polyelectrolyte," Langmuir 2005, 21, 10154.

Lu et al., "'Cyanine Pendant' Polymers on Nanoparticles and in Solution; Superquenching and Sensing Applications," Polym. Mat. Sci. Eng. 2002, 86, 17.

Lu et al., "Self-Assembled 'Polymers' on Nanoparticles: Superquenching and Sensing Applications," Polymer Preprints, 2002, 43, 124.

Luo et al., "Thermodynamic Stabilization Mechanism of Block Copolymer Vesicles," J. Am. Chem. Soc. 2001, 123(5), 1012.

Martin, et al., "Picosecond Laser Photolysis Studies of Deactivation Processes of Excited Hydrogen-Bonding Complexes. 2. Dibenxocarbazole-Pyridine Systems," J. Phys. Chem. 1982, 86, 4148-4156.

McGill, et al., "Choosing polymer coatings for chemical sensors," Chemtech 1994, 24, 27-37.

McQuade et al., "Two-Dimensional Conjugated Polymer Assemblies: Interchain Spacing for Control of Photophysics," J. Am. Chem. Soc. 2000, 122(24), 5885.

McQuade et al., "Conjugated Polymer-Based Chemical Sensors," Chem. Rev. 2000, 100(7), 2537.

Miao et al., "Fluorescence Sensory Polymers Containing Rigid Nonplanar Aromatic Scaffolds," Proceedings of the 1997 Boston meeting, vol. 39, No. 2, pp. 1081-1082, Aug. 23-27, 1998, Polym. Prepr. Div. Polym. Chem. Am .Chem .Soc.; Polymer Preprints, Division of Polymer Chemistry, American Chemical Society, Aug. 1998 ACS, Washington D.C.

Mitschke et al., "The electroluminescence of organic materials," J. Mater. Chem. 2000, 10, 1471.

Miyasaka, et al., "Femtosecond-Picosecond Laser Photolysis Studies on the Mechanisms of Fluorescence Quenching Induced by Hydrogen-Bonding Interactions—1-Pyrenol-Pyridine Systems," J. Phys. Chem. 1993, 97, 8222-8228.

Moon et al., "Capture and detection of a quencher labeled oligonucleotide by poly)phenylene ethy nylene) particles," Chem. Commun. 2003, 1, 104.

Norvez et al., "Epitaxygens: mesomorphic properties of triptycene derivatives," Liquid Crystals 1993, 14(5), 1389.

Oda et al., "Circularly Polarized Electroluminescence from Liquid-Crystalline Chiral Polyfluorenes," Adv. Mater. 2000, 12(5), 362.

Oda et al., "Chiroptical properties of chiral-substituted polyfluorenes," Synthetic Metals 2000, 111-112, 575.

Patel, et al., "Chemicapacitive microsensors for volatile organic compound detection," Sensors and Actuators B, 2003, 96, 541-553.

Peng et al., "Efficient Light Harvesting by Sequential Energy Transfer across Aggregates in Polymers of Finite Conjugational Segments with Short Aliphatic Linkages," J. Am. Chem. Soc. 2001, 123, 11388.

Peeters et al., "Circularly Polarized Electroluminescence from a Polymer Light-Emitting Diode," J. Am. Chem. Soc. 1997, 119(41), 9909.

Pinnaduwage, et al., "Detection of 2,4-dinitrotoluene using microcantilever sensors," Sensors and Actuators B, 2004, 99, 223-229.

Place et al., "Stabilization of the Aggregation of Cyanine Dyes at the Molecular and Nanoscopic Level," Langmuir 2000, 16(23), 9042.

Pschirer et al., "Poly(fluorenyleneethynylene)s by Alkyne Metathesis: Optical Properties and Aggregation Behavior," Macromolecules 2000, 33(11), 3961.

Rininsland et al., "High-Throughput Kinase Assays with Protein Substrates Using Fluorescent Polymer Superquenching," BMC Biotech. 2005, 5, 16.

Rininsland et al., "Metal Ion-Mediated Polymer Superquenching for Highly Sensitive Detection of Kinase and Phosphatase Activities," PNAS 2004, 101(43), 15295.

Snow et al., "Synthesis and Evaluation of Hexafluorodimethylcarbinol Functionalized Polymers as Microsensor Coatings," J. Applied Polymer Science 1991, 43, 1659-1671.

Swager et al., "Fluorescence Studies of Poly(p-phenyleneethynylene)s: The Effect of Anthracene Substitution," J. Phys .Chem. 1995, 99(14), 4886.

Swager, "The Molecular Wire Approach to Sensory Signal Amplification," Acc. Chem. Res. 1998, 31(5), 201.

Tan et al., "Photophysics, aggregation and amplified quenching of a water-soluble poly(phenylene ethynylene)," Chem. Commun. 2002, 446.

Thomas, III et al., "Conjugated Polymer Sensors: Design Principles Towards Enhanced Versatility," presented at the Army Science Conference, Dec. 2004.

Thomas, III et al., "Conjugated Polymer Sensors: Detection of DMNB and Hydrazine," presented to the American Chemical Society at the 230$^{th}$ National Meeting, Washington, D.C. (Aug. 28-Sep. 1, 2005).

Thomas, III et al., "Conjugated Polymer Sensors: Detection of DMNB and Hydrazine," presented at the Materials Research Symposium, Boston, MA (Dec. 2005).

Thomas, III et al., "Amplifying fluorescent polymer sensors for the explosives taggant 2,3-dimethyl-2,3-dinitrobutane (DMNB)," Chem. Commun. 2005, 4572-4574.

Thomas, III et al. "Trace Hydrazine Detection with Fluorescent Conjugated Polymers: A Turn-On Sensory Mechanism," Adv. Materials 2006, 18, 1047-1050.

Van Houten et al., "Rapid Luminescent Detection of Phosphate Esters in Solution and the Gas Phase Using (dppe)Pt{S2C2(2-pyridyl)(CH2CH2OH)}," J. Am. Chem. Soc. 1998, 120(47), 12359.

Walters et al., "Photophysical Consequences of Conformation and Aggregation in Dilute Solutions of π-Conjugated Oligomers," Langmuir 1999, 15, 5676.

Waluk, "Hydrogen-Bonding-Induced Phenomena in Bifunctional Heteroazaaromatics," Acc. Chem. Res. 2003, 36, 832-838.

Wang et al., "Fluorescein Provides a Resonance Gate for FRET from Conjugated Polymers to DNA Intercalated Dyes," J. Am. Chem. Soc. 2004, 126, 5446.

Wang et al., "Photoluminescence Quenching of Conjugated Macromolecules by Bipyridinium Derivatives in Aqueous Media: Charge Dependence," Langmuir 2001, 17, 1262.

Wang et al., "Photoluminescence of Water-Soluble Conjugated Polymers: Origin of Enhanced Quenching by Charge Transfer," Macromolecules 2000, 33, 5153.

Wang et al., "Biosensors from Conjugated Polyelectrolyte Complexes," PNAS 2002, 99(1), 49.

Weder et al., "Efficient Solid-State Photoluminescence in New Poly(2,5-dialkoxy-p-phenyleneethynylene)s," Macromolecules 1996, 29(15), 5157.

Whitten et al., "From Superquenching to Biodetection: Building Sensors Based on Fluorescent Polyelectrolytes," Chapter 4, *Optical Sensors and Switches*, New York: Marcel Dekker, 2001.

Wu et al., "Novel Nanoparticles Formed via Self-Assembly of Poly-(ethylene glycol-b-sebacic anhydride) and Their Degradation in Water," Macromolecules 2000, 33(24), 9040.

Xia et al., "Applications of Fluorescent Polymer Superquenching to High Throughput Screening Assays for Protein Kinases," Assay and Drug Dev. Tech. 2004, 2, 183.

Xia et al., "A High-Throughput Screening Assay for Kinases and Phosphatases via Metal Ion-Mediated Fluorescent Polymer Superquenching," American Laboratory 2004, 36, 15.

Yang et al., "Fluorescent Porous Polymer Films as TNT Chemosensors: Electronic and Structural Effects," J. Am. Chem. Soc. 1998, 120(46), 11864.

Yang et al., "Porous Shape Persistent Fluorescent Polymer Films: An Approach to TNT Sensory Materials," J. Am. Chem. Soc. 1998, 120(21), 5321.

Yang et al., "Anomalous crystal packing of iptycene secondary diamides leading to novel chain and channel networks," Tet. Lett. 2000, 41(41), 7911.

Zhang et al., "Formation of Novel Polymeric Nanoparticles," Acc. Chem. Res. 2001, 34(3), 249.

Zhang et al., "Fluorescent Detection of Chemical Warfare Agents: Specific Ratiometric Chemosensors," J. Am. Chem. Soc., vol. 125, pp. 3420-3423.

Zhang et al., "Fluorescent Detection of Chemical Warfare Agents: Functional Group Specific Ratiometric Chemosensors," Supporting Information, (http://pubs.acs.org/subscribe/journals/jacsat/suppinfo/ja029265z/ja029265zsi20030125_030500.pdf).

Zhou et al. "Fluorescent Chemosensors Based on Energy Migration in Conjugated Polymers: The Molecular Wire Approach to Increased Sensitivity," J. Am. Chem. Soc. 1995, 117(50), 12593.

Zhou et al., "Methodology for Enhancing the Sensitivity of Fluorescent Chemosensors: Energy Migration In Conjugated Polymers," J. Am. Chem. Soc. 1995, 117(26), 7017.

Institute for Soldier Nanotechnologies, (http://web.mit.edu/isn/industryday/index.html).

\* cited by examiner

P1a: R = C8H17
P1b: R = C10H21

P2

P3

P4

P5

P6

P7

US 8,158,437 B2

LUMINESCENT DETECTION OF HYDRAZINE AND HYDRAZINE DERIVATIVES

STATEMENT REGARDING FEDERALLY SPONSORED RESEARCH OR DEVELOPMENT

This invention was made with government support under Grant Number DE-AC04-94AL85000 awarded by the Department of Energy. The government has certain rights in this invention.

FIELD OF THE INVENTION

The present invention relates to methods for the determination of various explosives and toxins. The present invention also relates to methods for increasing the luminescence intensity of polymers.

BACKGROUND OF THE INVENTION

Sensory devices based on amplified fluorescence quenching of solid-state conjugated polymer films can be highly sensitive, due to the amplification that arises from delocalized excitons sampling many potential binding sites within one excited state lifetime. Previous work has demonstrated highly sensitive detection schemes using these amplifying fluorescent polymers for a number of analytes in solution and vapor phase, as described in U.S. Publication No. 2003/0178607. For example, sensors for the ultratrace detection of high explosives such as 2,4,6-trinitrotoluene (TNT) have been shown to display high sensitivity comparable to that of trained canines. In many cases, the transduction mechanism is photoinduced charge transfer (PICT) from a polymer donor to a substantially planar analyte that binds via a tight pi-complex to the conjugated polymer. For example, TNT is a planar, nitroaromatic molecule that can readily form a pi-complex with a conjugated polymer via pi-stacking interactions.

Although planar and/or aromatic compounds are often present in many explosives, present day security is in need of systems capable of matching comprehensive vapor phase detection of a broader range of high explosives and toxins. For example, the taggant 2,3-dimethyl-2,3-dinitrobutane (DMNB) is a required additive in all legally manufactured plastic explosives. DMNB has been previously detected using ion mobility spectrometry, a reliable but less sensitive technique relative to amplifying fluorescent polymers. DMNB has also been detected using other methods such as electron capture mass spectrometry which involve bulky and often complex machinery.

Hydrazine ($NH_2NH_2$), a heavily used industrial chemical, has been implicated as a carcinogen and is readily absorbed through the skin. Its strong reducing power has led to its use as an oxygen scavenger and corrosion inhibitor in various applications involving water-heating systems, as well as a fuel in rocket propulsion systems. As a result of its toxicity and reactivity, facile detection of hydrazine is also relevant to homeland security. Traditional analytical methods utilized for hydrazine detection include spectrophotometric detection, as well as assorted electrochemical schemes.

Accordingly improved methods are needed.

SUMMARY OF THE INVENTION

The present invention provides methods for determination of 2,3-dimethyl-2,3-dinitrobutane (DMNB), comprising exposing a luminescent polymer to a sample suspected of containing DMNB, wherein DMNB, if present, interacts with the luminescent polymer to cause a change in the luminescence of the polymer and determining the change in the luminescence of the polymer, thereby determining DMNB.

The present invention also provides methods for determination of hydrazine or hydrazine derivatives, comprising exposing a luminescent polymer to a sample suspected of containing hydrazine or hydrazine derivatives, wherein hydrazine or the hydrazine derivative, if present, interacts with the luminescent polymer to cause an increase in the luminescence intensity of the polymer, determining the increase in luminescence intensity of the polymer, thereby determining hydrazine or the hydrazine derivative.

The present invention also provides methods for increasing the luminescence intensity of a polymer, comprising exposing a luminescent polymer to hydrazine or the hydrazine derivative, wherein, in the absence of hydrazine or the hydrazine derivative, the luminescent polymer comprises non-radiative pathways, and, in the presence of hydrazine or the hydrazine derivative, hydrazine or the hydrazine derivative interacts with the luminescent polymer to reduce the number of non-radiative pathways, thereby increasing the luminescence intensity of the polymer.

DETAILED DESCRIPTION

Figure 1:
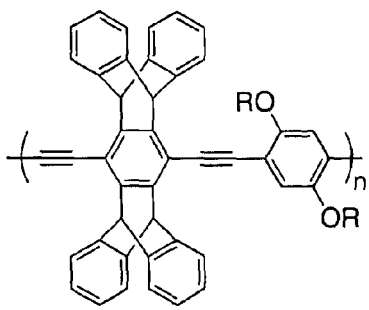
FIG. 1 shows luminescent polymers, according to some embodiments of the invention.
Figure 1:
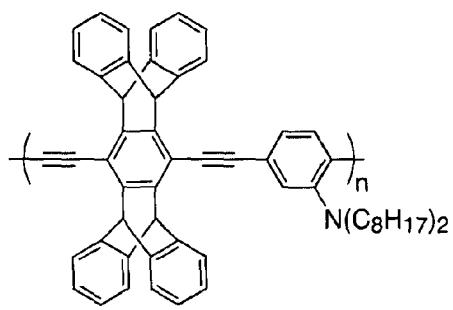
Figure 1:
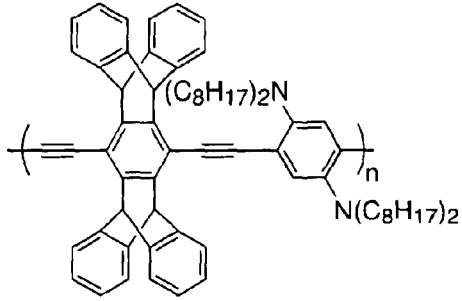
Figure 1:
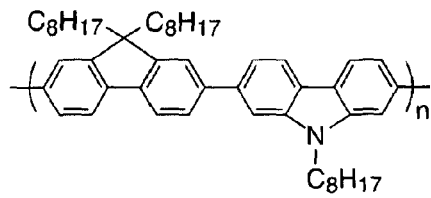
Figure 1:
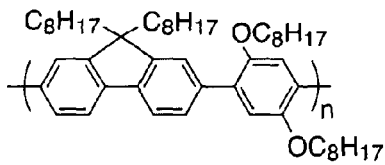
Figure 1:
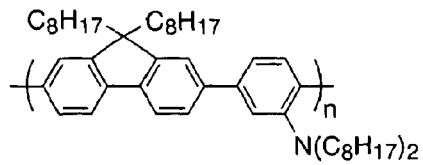
Figure 1:
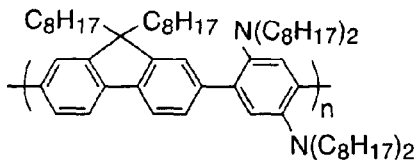

The present invention generally relates to methods for modulating the optical properties of a luminescent polymer via interaction with a species (e.g., an analyte).

In some cases, the present invention provides methods for determination of an analyte. The analytes may be determined by monitoring, for example, a change in an optical signal of a luminescent material (e.g., polymer) upon exposure to an analyte. In some cases, the present invention may be used for the vapor phase detection of analytes such as explosives and toxins. Methods of the present invention may be advantageous in that the high sensitivity of luminescence (e.g., fluorescence) spectroscopy can allow for the reliable detection of small changes in luminescence intensity. The present invention also provides methods for increasing the luminescence intensity of a polymer, such as a polymer that has been photobleached, by exposing the luminescent polymer to a species such as a reducing agent.

Methods for the determination of analytes (e.g., non-planar analytes, non-aromatic analytes) may comprise exposure of a luminescent polymer to a sample suspected of containing the analyte, and, if present, the analyte interacts with the luminescent polymer to cause a change in the luminescence of the polymer. The change in the luminescence of the polymer may then determine the analyte. In some cases, the change comprises a decrease in luminescence intensity. In some cases, the change comprises an increase in luminescence intensity. As used herein, the term "determining" generally refers to the analysis of a species or signal, for example, quantitatively or qualitatively, and/or the detection of the presence or absence of the species or signals. "Determining" may also refer to the analysis of an interaction between two or more species or signals, for example, quantitatively or qualitatively, and/or by detecting the presence or absence of the interaction. The materials and methods described herein may be incorporated into devices such as sensors or any device or article capable of detecting an analyte. In some embodiments, the analyte (e.g., DMNB, hydrazine) may be determined when present in only trace quantities.

The present invention may be particularly advantageous in that analytes which do not readily form pi-stacking interactions with conjugated polymers may be; determined. As used herein, "pi-stacking interactions" refer to cofacial interactions between pi-orbitals of conjugated species. Examples of such analytes include those which are, for example, non-planar, non-aromatic, and/or have relatively high reduction potentials (i.e., weak electron affinity). The taggant 2,3-dimethyl-2,3-dinitrobutane (DMNB) may be characterized by a non-planar, three-dimensional structure and a reduction potential of −1.7 V (versus standard calomel electrode, SCE), making it difficult for DMNB to engage in pi-stacking interactions with luminescent polymers having pi-conjugated moieties. Other explosives may include RDX (hexahydro-1,3,5-trinitro-1,3,5-triazine), PETN (2,2-bis[(nitrooxy)-methyl]-1,3-propanediol dinitrate (ester)), other nitro- or nitrate-containing species, and the like. Methods of the invention may also be advantageous for various toxins including strong reducing agents, such as hydrazine and hydrazine derivatives.

The interaction between the luminescent polymer and the analyte may comprise, for example, energy transfer (e.g., photoinduced charge transfer, fluorescence resonance energy transfer), electrostatic interactions, binding interactions, redox reactions (e.g., reduction, oxidation), other chemical reactions, and the like. In some cases, the analyte may be an electron acceptor and the luminescent polymer may be an electron donor. In some cases, the analyte may be an electron donor and the luminescent polymer may be an electron acceptor. In some embodiments, the analyte may also act as a reducing agent to increase the luminescence intensity of a polymer.

In some embodiments, the interaction between the luminescent polymer and the analyte comprises photoinduced charge transfer, wherein an excited-state polymer transfers an electron to an analyte (e.g., DMNB). For example, the luminescent polymer may form an excited state upon exposure to electromagnetic radiation and produce a first emission signal. In the excited-state, the luminescent polymer may then interact with (e.g., transfer charge to) an analyte, resulting in a second emission which has decreased or "quenched" luminescence intensity (e.g., a "turn-off" detection mechanism). In an illustrative embodiment shown in FIG. 3, a film of polymer P5 exhibits a decrease in fluorescence emission intensity upon repeated variable time exposures to DMNB vapor.

Figure 9:
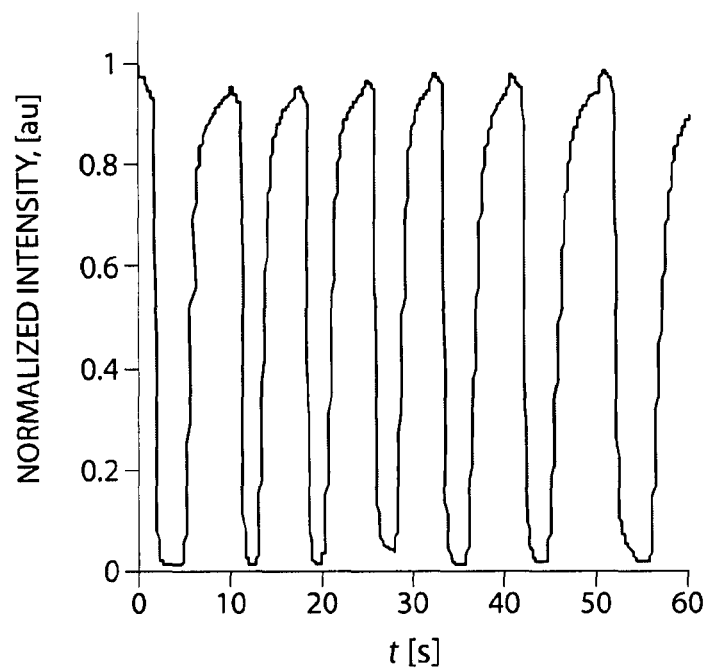
FIG. 9 shows a plot of normalized emission intensity of a film of P3 as a function of time upon exposure to saturated iodine vapor (quench) followed by saturated hydrazine vapor (recovery).

Alternatively, the interaction between the luminescent polymer and the analyte may comprise a chemical reaction such as a reduction reaction which may increase the luminescence intensity of the polymer. The luminescent polymer may exist in a "quenched" state and have substantially no emission signal upon exposure to electromagnetic radiation, wherein, upon interaction with an analyte, the analyte may interact with (e.g., reduce) at least a portion of the luminescent polymer and/or a quenching molecule associated with the luminescent polymer such that an emission signal is generated that has a greater luminescence intensity than the emission signal in the absence of analyte upon exposure to the same conditions of electromagnetic radiation (e.g., a "turn-on" detection mechanism). FIG. 9 shows an illustrative embodiment, wherein an $I_2$-doped (i.e., fluorescence quenched) film of polymer P3 shows an increase in fluorescence emission upon exposure to hydrazine vapor over multiple $I_2$/hydrazine exposure cycles.

In some cases, methods of the invention comprise determining a change in the wavelength of an emission signal. The wavelength of an emission signal refers to the wavelength at which the peak maximum of the emission signal occurs in ah emission spectrum. The emission signal may be a particular peak having, the largest intensity in an emission spectrum (e.g. a fluorescence spectrum), or, alternatively, the emission signal may be a peak in an emission spectrum that has at least a defined maximum, but has a smaller intensity relative to other peaks in the emission spectrum.

In some embodiments, the change in luminescence intensity may occur for an emission signal with substantially no shift in the wavelength of the luminescence (e.g., emission), wherein the intensity of the emission signal changes but the wavelength remains essentially unchanged. In other embodiments, the change in luminescence intensity may occur for an emission signal in combination with a shift in the wavelength of the luminescence (e.g., emission). For example, an emission-signal may simultaneously undergo a shift in wavelength in addition to an increase or decrease in luminescence intensity. In another embodiment, the change may comprise two emission signals occurring at two different wavelengths, wherein each of the two emission signals undergoes a change in luminescence intensity. In some cases, the two emission signals may undergo changes in luminescence intensity independent of one another. In some cases, the two emission signals may undergo changes in luminescence intensity, wherein the two emission signals are associated with one another, for example, via an energy transfer mechanism, as described more fully below.

In some embodiments, methods of the present invention may further comprise determining a change in the wavelength of the luminescence upon exposure of a luminescent polymer to an analyte. That is, in some cases, determination of an analyte may comprise observing a change in luminescence intensity in combination with a change in the luminescence wavelength. For example, the relative luminescence intensities of a first emission signal and a second emission signal associated with the first emission signal may be modulated using the quenching and unquenching methods described herein. In some cases, the first emission signal and the second emission signal may be associated with (e.g., interact with) one another via an energy transfer mechanism, such as fluorescence resonance energy transfer, for example. The term "fluorescence resonance energy transfer" or "FRET" is known in the art and refers to the transfer of excitation energy from an excited state species (i.e., FRET donor) to an acceptor species (i.e., FRET acceptor), wherein an emission is observed from the acceptor species. In some cases, the FRET donor may be a luminescent polymer, portion(s) thereof, or other species, such as an analyte. Similarly, the FRET acceptor may be a luminescent polymer, portion(s) thereof, or other species, such as an analyte.

In one embodiment, a first portion of a luminescent polymer may act as FRET donor and a second portion within the same luminescent polymer may act as a FRET acceptor, wherein the first portion and the second portion each have different emission wavelengths. The luminescent polymer may be associated with a quenching molecule and exist in a "quenched" state, wherein, upon exposure of the first portion to electromagnetic radiation, the quenching molecule absorbs the excitation energy and substantially no emission is observed. Upon exposure to an analyte, the analyte may interact with the luminescent polymer and/or quenching molecule to "un-quench" the luminescent polymer. As a result, exposure of the first portion to electromagnetic radiation produces an excited-state, wherein the first portion of the luminescent polymer may transfer excitation energy to the second portion of the luminescent polymer, and emission signal from the second portion is observed.

Figure 2A:
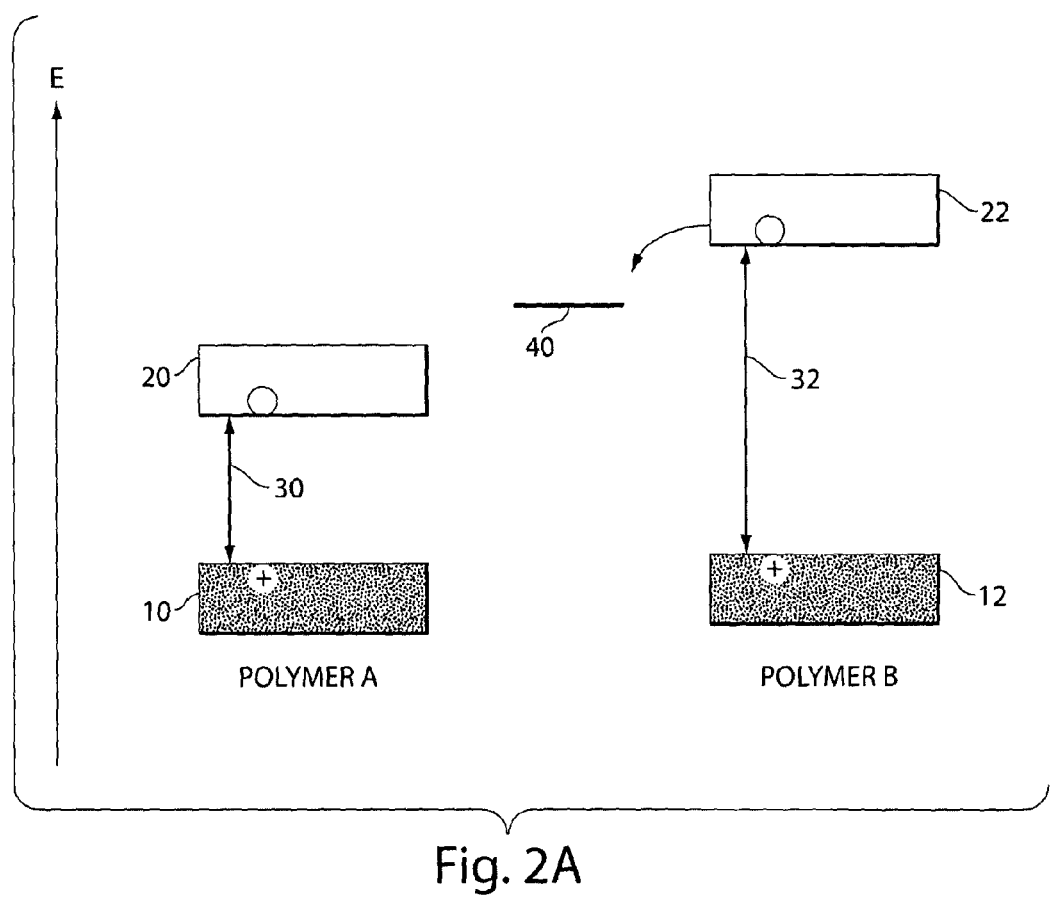
FIG. 2 shows a schematic representation of qualitative energy level diagrams of the valence bands and conduction bands of polymers, according to some embodiments of the invention.

The properties of luminescent polymers of the invention may be tailored to suit a particular application, such as determination of a particular analyte. In some embodiments, the luminescent polymer may be designed interact with an analyte having high reduction potential (e.g., a high energy LUMO). For example, the band gap of a luminescent polymer may be designed to energetically favor interaction (e.g., photoinduced charge transfer) with an analyte. FIG. 2A shows the "band gap" of a pi-conjugated polymer which, as used herein, refers to the energy difference 30 between the valence band 10 and the conduction band 20. In the excited-state, electrons in the conduction band may be transferred to a species having a LUMO 40, which is lower in energy relative to the conduction band 20. As shown in FIG. 2A, polymer A has a conduction band which is lower in energy than the LUMO 40 of an analyte, making energy transfer from the excited-state polymer to the analyte energetically unfavorable. In contrast, polymer B has as conduction band which is higher in energy than the LUMO 40 of the analyte, making energy transfer from the excited-state polymer to the analyte energetically favorable.

The band gap of the luminescent polymer may be tailored such that the conduction band of the luminescent polymer is higher in energy than the LUMO of the analyte, producing a material having increased excited-state reduction potential that allows the polymer to transfer charge to the analyte in an energetically favorable manner. In some cases, a wider band gap may enable more exergonic electron transfer from a higher energy conduction band to the LUMO of an analyte. The band gap may be tailored by functionalizing the luminescent polymer with groups that either donate or accept electron density, as described more fully below. For example, the luminescent polymer may be substituted with electron-donating groups to increase the electron density and raise the conduction band of the polymer.

Figure 2B:
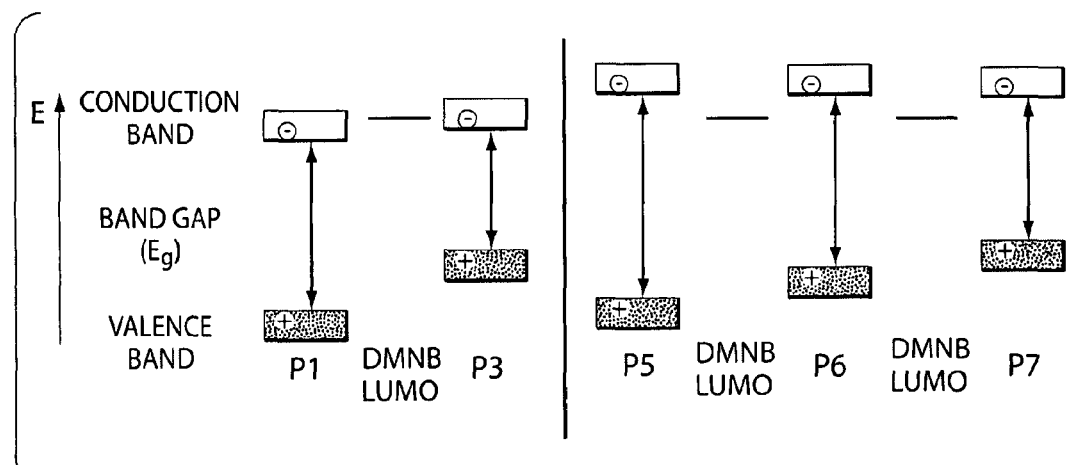

FIG. 1 shows examples of some luminescent polymers that may be used in the determination of DMNB. Polymers P1-P3 are poly(aryleneethylnylene)s comprising rigid, non-planar iptycene groups substituted with electron-donating alkoxy or disubstituted-amine groups. FIG. 2B shows a schematic representation of qualitative energy level diagrams of the valence bands and conduction bands of P1 and P3. As shown in FIG. 2B, dialkoxy-substituted polymer P1 has a larger band gap than diamino-substituted polymer P3. While increasing amine-substitution for polymers P1-P3 raises the energy of both the conduction band (e.g., LUMO) and the valence band (e.g., HOMO), the valence bands for polymers P1-P3 display greater increases in energy such that increasing amine-substitution results in a smaller band gap for P3, relative to P1 and P2.

In some embodiments, the band gap may be tailored by varying the three-dimensional structure of the luminescent polymer. For example, the luminescent polymer may comprise monomers which are non-planar with respect to adjacent monomers to produce a twisted backbone having a non-planar ground state conformation. The twisted or non-planar polymer backbone may lead to decreased conjugation and a higher energy conduction band. The twisting of the polymer backbone may be enhanced by employing monomers substituted with, for example, sterically large pendant groups, as described more fully below.

As an illustrative embodiment shown in FIG. 1, polymers P4-P7 are poly(phenylene)s that are optically blue-shifted relative to polymers P1-P3 due to a non-planar ground state conformation with decreased conjugation. In some cases, the more blue-shifted poly(phenylene)s may be quenched by DMNB with diffusion controlled rate constants. Also, increasing amine-substitution for polymers P4-P7 raises the valence band (e.g., HOMO) levels and has a smaller perturbation on the conduction band (e.g., LUMO) energies, which lowers the band gap.

In some cases, the luminescent polymer may be a poly(arylene), poly(arylenevinylene), poly(aryleneethylnylene), or substituted derivatives thereof. In some embodiments, the luminescent polymer is a poly(aryleneethylnylene). In some embodiments, the luminescent polymer is poly(arylene), such as poly(phenylene).

In one set of embodiments, additional determination methods may be used in combination with methods of the present invention. Confirmatory chemistry may be incorporated into a sensory device to discriminate DMNB from pother potential quenchers. For example, in the presence of electromagnetic radiation DMNB may undergo reductive cleavage to generate a nitrite ion, which may be detected via a colorimetric tests as known to those of ordinary skill in the art. Generation of the nitrite ion is generally unique to DMNB, relative to other quenching analytes (e.g., TNT), such that the identity of DMNB may be confirmed in addition to the determination of the presence and/or amount of analyte by luminescence quenching methods.

Another embodiment of the invention comprises methods for determining the toxin hydrazine and other species comprising a hydrazine moiety. In some embodiments, the method comprises a "turn-on" detection mechanism, wherein the luminescent polymer is "quenched" in the absence of analyte and emits a luminescent signal in the presence of analyte. For example, a luminescent polymer may comprise non-radiative pathways in the absence of analyte, resulting in a decreased luminescence emission. In the presence of hydrazine or the hydrazine derivative, the hydrazine or the hydrazine derivative can interact with the luminescent polymer to reduce the number of non-radiative pathways, thereby increasing the luminescence intensity of the material. Hydrazine derivatives may include alkyl-substituted hydrazines; other hydrazine-containing species, and the like.

As used herein, an excited-state molecule may return (e.g., "relax") to the ground state via a "non-radiative" pathway, in which the excitation energy is dissipated as energy other than electromagnetic radiation, such as heat, for example. In a "radiative" pathway, an excited-state molecule may return to the ground state by emitting the excitation energy as electromagnetic radiation (e.g., fluorescence emission). In some cases, relaxation of an excited-state luminescent polymer can occur through a non-radiative pathway via the existence of a small number of oxidized sites within the polymer itself. In some cases, relaxation or quenching of an excited state can occur through a non-radiative pathway via interaction with a second molecule (e.g., a quencher). For example, molecular oxygen or molecular iodine are efficient quenchers of fluorescence. The intentional introduction of iodine or oxygen as a reducable quencher and oxidant within a sample (e.g., film) of luminescent polymer may reduce the intensity of the background fluorescence signal in trace detection experiments.

Upon exposure to hydrazine (or hydrazine derivative) vapor, the quenched luminescent polymer may be "unquenched" by reduction of either quenching molecules associated with the polymer and/or oxidized sites within the polymer itself to give large increases in luminescence intensity. This type of "unquenching" mechanism is essentially the reverse of amplified detection by fluorescence quenching of conjugated polymer films in response to electron poor analytes.

In some cases, methods of the invention may be advantageous in that the hydrazine detection scheme relies upon reduction of the luminescent polymer as the transduction mechanism. That is, the hydrazine or hydrazine-containing species is a strong reducing agent capable of reducing the quencher molecule and/or oxidized sites of a luminescent polymer at low concentrations, whereas other amines (e.g., ammonia), organic solvents (e.g., tetrahydrofuran, methanol, etc), or other common interferents of the hydrazine detection scheme may not be strong interferents at low concentrations. For example, exposure of a luminescent polymer to a 50 ppm concentration of ammonia gives a luminescence signal increase (20%) at least an order of magnitude less than that observed with 1 ppm hydrazine.

In some embodiments, the luminescent polymer may be designed to interact with an analyte that is a strong reducing agent, such as hydrazine, by functionalizing the polymer with groups that donate electron density, such as amines, for example. Electron-rich luminescent polymers may be easily oxidized and may give large emission enhancement upon exposure to hydrazine. FIG. 1 shows examples of some luminescent polymers that may be useful in the determination of hydrazine and hydrazine derivatives (e.g., P1-P3). Polymer P3, which is more electron-rich and more readily oxidized relative to polymer P1 and P2 may give larger on/off ratios upon exposure to hydrazine.

In addition, hydrazine vapor may be used to regenerate species which have been oxidized or photobleached. For example, hydrazine exposure of functional conjugated polymer films (e.g. for explosives detection) that have lost a portion of their solid-state emission due to aging or photobleaching may allow for the extension of their useful lifetimes.

The present invention provides methods for increasing the luminescence intensity of a polymer, comprising exposing a luminescent polymer to hydrazine or the hydrazine derivative, wherein, in the absence of hydrazine or the hydrazine derivative, the luminescent polymer comprises non-radiative pathways, and, in the presence of hydrazine or the hydrazine derivative, hydrazine or the hydrazine derivative interacts with the luminescent polymer to reduce the number of non-radiative pathways, thereby increasing the luminescence intensity of the material.

In some cases, upon exposure to hydrazine or a hydrazine derivative, the luminescence intensity of the polymer increases by at least 25% relative to the luminescence intensity of the polymer in the absence of hydrazine or the hydrazine derivative upon exposure to the same conditions of electromagnetic radiation. In some cases, in the presence of hydrazine or the hydrazine derivative, the luminescence intensity increases by at least 50%, 75%, 100%, 250%, 500%, 750%, or 1000% relative to the luminescence intensity in the absence of hydrazine or the hydrazine derivative upon exposure to the same conditions of electromagnetic radiation.

As described herein, some embodiments of the present invention comprise the use of luminescent polymers as described herein for determination of an analyte. In some embodiments, the invention comprises the use of luminescent polymers for the determination of DMNB. In some embodiments, the invention comprises the use of luminescent polymers for the determination of hydrazine and hydrazine derivatives. It should be understood that the luminescent polymers as described herein may be useful in determination of one or more analytes.

For example, in one set of embodiments, the invention comprises the use of poly(arylene)s for the determination of DMNB. Some embodiments of the present invention comprise a luminescent polymer having the structure,

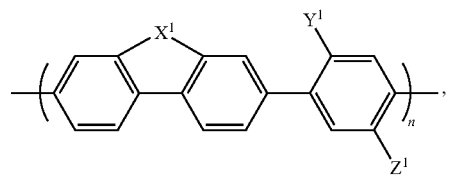

wherein $X^1$ is carbon or heteroatom, and $X^1$ optionally carries an alkyl substituent, $Y^1$ and $Z^1$ are independently hydrogen, alkyl, or heteroalkyl; and n is greater than 1. As used herein, "heteroatom" is given its ordinary meaning in the art and refers to an atom of any element other than carbon or hydrogen. Illustrative heteroatoms include boron, nitrogen, oxygen, phosphorus, sulfur and selenium, and alternatively oxygen, nitrogen or sulfur. In some cases, the heteroatom is oxygen or nitrogen. In some embodiments, the heteroatom is nitrogen. In some embodiments, at least one of $Y^1$ and $Z^1$ is a dialkyl-substituted amine. In some embodiments, at least one of $Y^1$ and $Z^1$ is an alkoxy group. In a particular embodiment, $X^1$ is dialkyl-substituted carbon, $Y^1$ is hydrogen, and $Z^1$ is dialkyl-substituted amine. In another particular embodiment, $X^1$ is dialkyl-substituted carbon and $Y^1$ and $Z^1$ are dialkyl-substituted amine. FIG. 1 shows some examples of such polymers (e.g., polymers P5-P7).

Other embodiments of the present invention comprise a luminescent polymer having the structure,

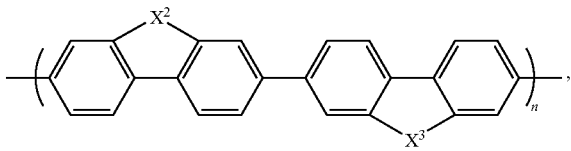

wherein $X^2$ and $X^3$ are independently carbon or heteroatom, and $X^2$ and $X^3$ optionally carry an alkyl substituent, and n is greater than 1. In one embodiment, $X^2$ and $X^3$ are dialkyl-substituted carbon. In one embodiment, $X^2$ is dialkyl-substituted carbon and $X^3$ is dialkyl-substituted amine. In one embodiment, $X^2$ and $X^3$ are dialkyl-substituted amine.

Some embodiments of the invention comprise the use of luminescent polymer for the determination of hydrazine and hydrazine derivatives. The luminescent polymer may have the structure,

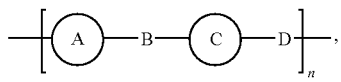

wherein n is at least 1, A and C are optionally substituted aromatic groups, and B and D are alkene, alkyne, heteroalkene, or heteroalkene. In other embodiments of the invention, poly(phenylene ethynylene)s may be used, wherein B and D are alkynes.

In some cases, the luminescent polymer has the structure,

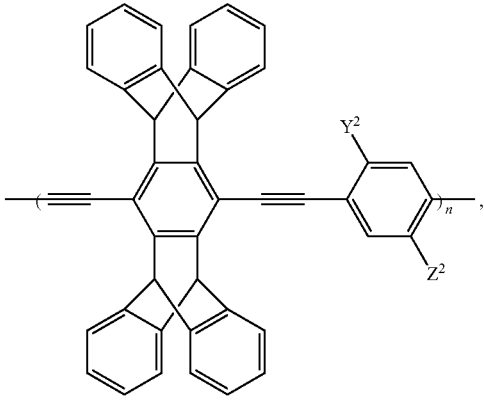

wherein $Y^2$ and $Z^2$ are independently alkyl, alkoxy, amino, and substituted derivatives thereof. In one embodiment, $Y^2$ and $Z^2$ are alkoxy. In another embodiment, $Y^2$ and $Z^2$ are $NR^1R^2$, wherein $R^1$ and $R^2$ are alkyl. In another embodiment, $Y^2$ is hydrogen and $Z^2$ is $NR^1R^2$, wherein $R^1$ and $R^2$ are alkyl. FIG. 1 shows some examples of such polymers (e.g., polymers P1-P3).

In some cases, the luminescent polymer may comprise one or more; heterocycle groups, optionally substituted, within the polymer backbone and/or a pendant group to the polymer backbone. The heterocycle may be bonded to the polymer backbone (e.g., an aryl group of the polymer backbone), or a group that is pendant to the polymer backbone, via a carbon atom and/or a heteroatom. The term "heterocycle" is given its ordinary meaning in the art and refers to cyclic groups containing at least one heteroatom as a ring atom, such as oxygen, sulfur, nitrogen, phosphorus, and the like, as described more fully below. In some cases, the heterocycle is a nitrogen heterocycle, such as pyrazine, pyrimidine, pyrrole, or triazole. In some cases, the heterocycle is an oxygen heterocycle, such as furan or tetrahydrofuran.

In one set of embodiments, the luminescent polymer may comprise a triazole group, optionally substituted. In some cases, the luminescent polymer has a polymer backbone comprising a triazole group, optionally substituted. In some cases, the luminescent polymer comprises a pendant group comprising a triazole group, optionally substituted. The triazole group may be bonded to the luminescent polymer via a carbon atom and/or a nitrogen atom. For example, in some embodiments, the luminescent polymer has the structure,

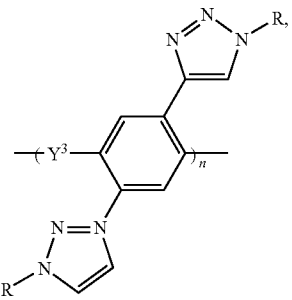

wherein $Y^3$ is alkene, alkyne, aryl, heteroalkene, heteroalkyne, or heteroaryl, optionally substituted; R is aryl or alkyl, optionally substituted; and n is greater than 1. Luminescent polymers comprising heterocycles, as described herein, may be useful in the determination of analytes including DMNB, hydrazine, and hydrazine derivatives.

It should be understood that polymers of the invention may be further substituted with additional functional groups, as described herein.

As used herein, a "luminescent polymer" refers to a polymer that can absorb a quantum of electromagnetic radiation to cause the polymer to achieve an excited state structure. Luminescent polymers may also be capable of emitting radiation. Radiation can be emitted from the polymer or from a chromophore associated with (e.g., covalently bound to, non-covalently bound to, etc.) the polymer. The emitted radiation may be luminescence, in which "luminescence" is defined as an emission of ultraviolet or visible radiation. Specific types of luminescence include "fluorescence" in which a time interval between absorption and emission of visible radiation ranges from $10^{-12}$ to $10^{-7}$ s. "Chemiluminescence" refers to emission of radiation due to a chemical reaction, whereas "electrochemiluminescence" refers to emission of radiation due to electrochemical reactions. Typically, the extent of delocalized bonding allows the existence of a number of accessible electronic excited states. If the conjugation is so extensive so as to produce a near continuum of excited states, electronic excitations can involve a valence band, the highest fully occupied band, and a conduction band, often referred to as a band gap, as described herein.

Luminescent polymers may be used in various detection schemes for the determination of analytes. In some cases, the luminescent polymer may be used in a "turn-off" detection mechanism, wherein, in the presence of analyte, the excited state of a luminescent polymer interacts with the analyte via photoinduced electron transfer to "quench" the luminescence (e.g., fluorescence, phosphorescence, etc.) of the polymer.

"Quenching" of luminescence may occur when a chromophore such as a luminescent polymer in an excited state is exposed to an "acceptor" species that can absorb energy from the excited state chromophore. The excited state chromophore returns to a ground state due to nonradiative processes (i.e. without emitting radiation), resulting in a reduced quantum yield. A "quantum yield" refers to a number of photons emitted per adsorbed photon. Thus, the excited state chromophore can function as a "donor" species in that it transfers energy to the acceptor species. The acceptor species can be an external molecule (e.g., analyte) or an internal species such as another portion of the same polymer. For example, a "turn-off" detection method may be used to determine the presence and/or amount of DMNB, as described more fully below. Alternatively, the luminescent polymer may be used in a "turn-on" detection mechanism, wherein, in the absence of analyte, the luminescent polymer may exist in a quenched state and substantially no emission signal, or a significantly reduced emission signal is observed. In the presence of analyte, the polymer may interact with the analyte to produce an emission. This process may be referred to as a "turn-on" luminescence detection method. For example, a "turn-on" detection method may be used to determine the presence and/or amount of hydrazine or derivatives of hydrazine, as described herein. In some cases, the "turn-on" fluorescence sensory scheme may be preferred since there are often fewer potential interferents that could cause a false positive with an emission increase or "turn-on" detection scheme.

Polymers, as used herein, refer to extended molecular structures comprising a backbone (e.g., non-conjugated backbone, conjugated backbone) which optionally contain pendant side groups, where "backbone" refers to the longest continuous bond pathway of the polymer. In one embodiment, at least a portion of the polymer is conjugated or pi-conjugated, i.e. the polymer has at least one portion along which electron density or electronic charge can be conducted, where the electronic charge is referred to as being "delocalized." Each p-orbital participating in conjugation can have sufficient overlap with adjacent conjugated p-orbitals. In one embodiment, at least a portion of the backbone is conjugated. In one embodiment, the entire backbone is conjugated and the polymer is referred to as a "conjugated polymer." Polymers having a conjugated pi-backbone capable of conducting electronic charge may be referred to as "conducting polymers." In some cases, the conjugated pi-backbone may be defined by a plane of atoms directly participating in the conjugation, wherein the plane arises from a preferred arrangement of the p-orbitals to maximize p-orbital overlap, thus maximizing conjugation and electronic conduction. In some cases, the pi-backbone may preferably have a non-planar or twisted ground state conformation, leading to decreased conjugation and a higher energy conduction band.

In one embodiment, the polymer is selected from the group consisting of polyarylenes, polyarylene vinylenes, polyarylene ethynylenes and ladder polymers, i.e. polymers having a backbone that can only be severed by breaking two bonds. Examples of such polymers include polythiophene, polypyrrole, polyacetylene, polyphenylene and substituted derivatives thereof.

Figure 10:
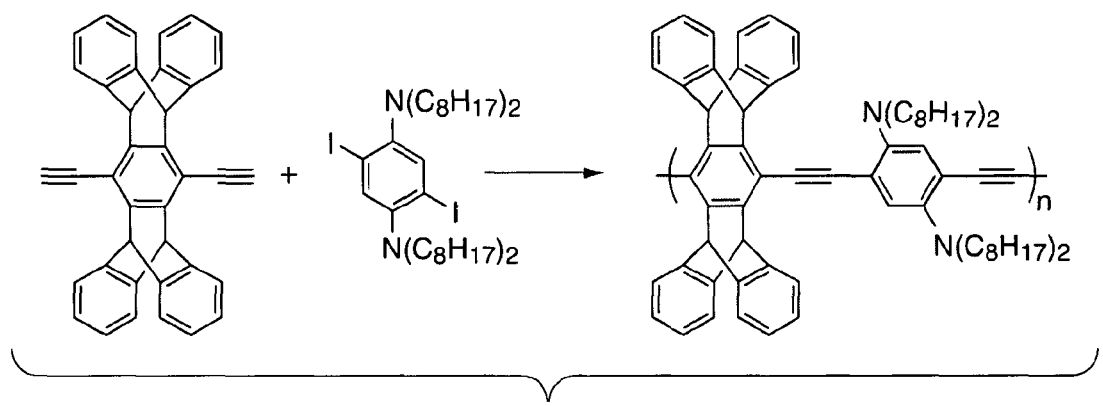
FIG. 10 shows an illustrative embodiment of a synthetic scheme for synthesizing poly(phenylene ethynylene)s, according to one embodiment of the invention.

The luminescent polymers as described herein may by synthesized using known methods, such as those disclosed in Yang, et al., *J. Am. Chem. Soc.* 1998, 120, 12389; Thomas III, et al., *Macromolecules* 2005, 38, 2716; Morin, et al., *Macromolecules* 2001, 34, 4680, incorporated herein by reference. For example, FIG. 10 shows an illustrative embodiment of a synthetic scheme for synthesizing poly(phenylene ethynylene)s, wherein polymerization of a di-halide containing monomer and a di-acetylene-containing monomer via a metal-catalyzed Sonogashira cross-coupling reaction can produce the polymer. Poly(phenylene)s may be synthesized using known methods, such as those disclosed in Lamba, et al., *J. Am. Chem. Soc.* 1994, 116, 11723 and Bredas, et al., *Polym. Prepr. (Am. Chem. Sco., Div. Polym. Chem.)* 1994, 35, 185, incorporated herein by reference.

Figure 11A:
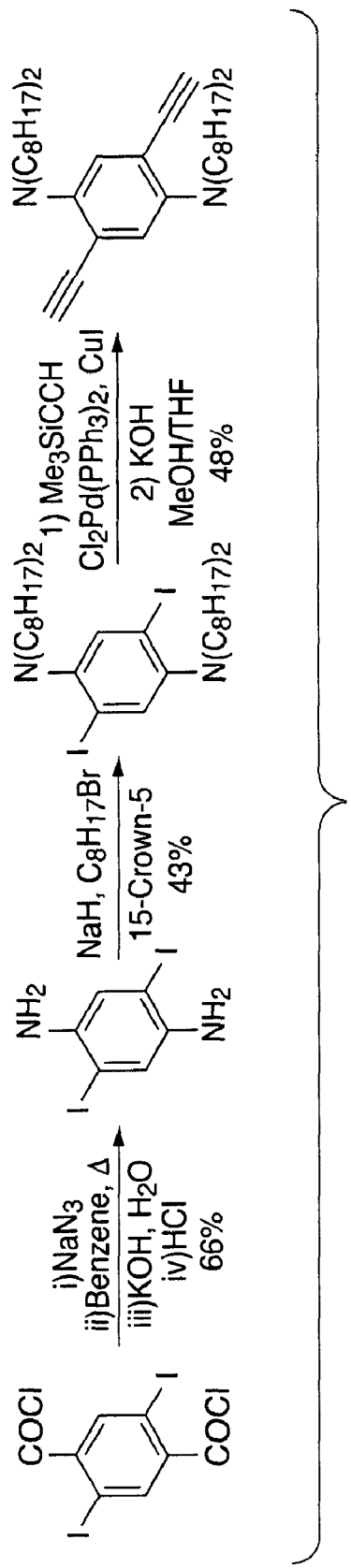
FIG. 11 shows several illustrative embodiments for the synthesis of electron-rich monomers containing amine groups.
Figure 11B:
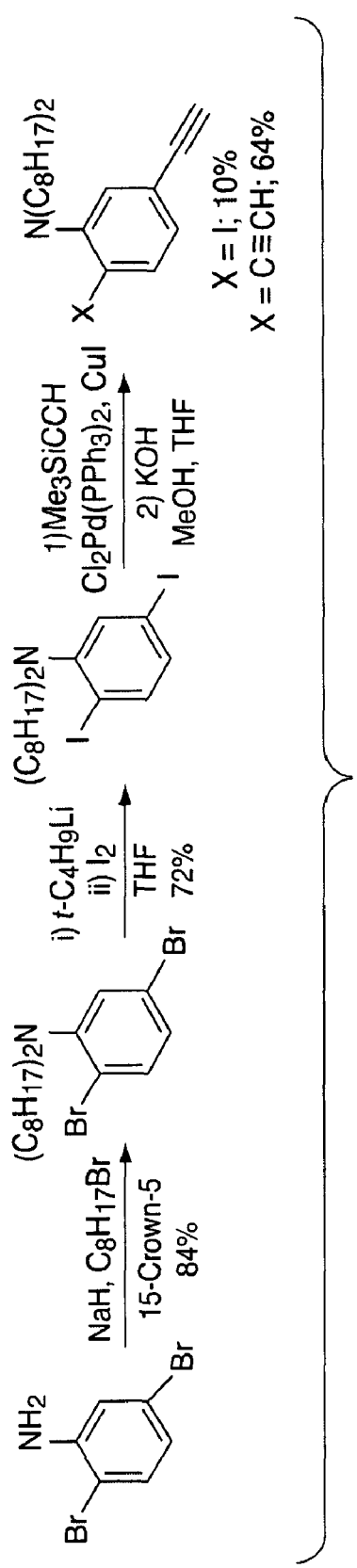
Figure 11C:
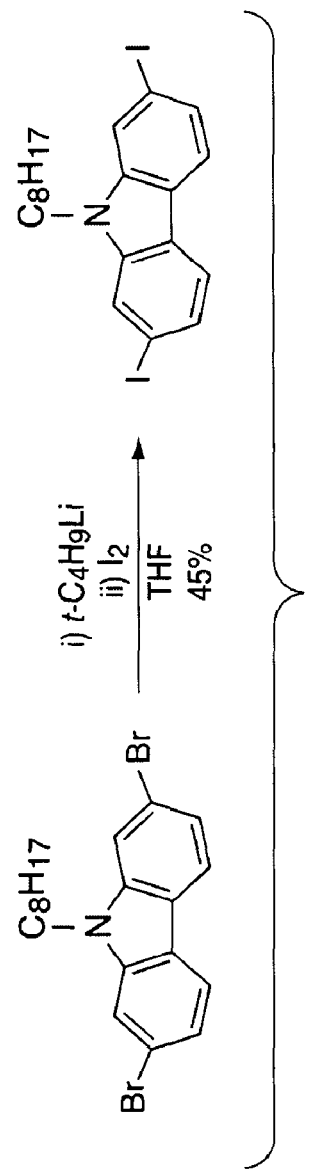

The properties of the luminescent polymers may also be tuned based on the substitution of the conjugated polymer backbone. Those skilled in the art would recognize what types of functional groups would afford a particular, desired property, such as a particular band gap, as described herein, or a specific emission wavelength. For example, the polymer may be substituted with electron-poor groups, such as acyl, carboxyl, cyano, nitro, sulfonate, or the like, or the polymer may install electron-poor aryl groups in the backbone of the polymer, such that the polymer exhibits fluorescence emission at shorter wavelengths. In other embodiments, the monomers may be substituted with electron-rich groups, such as amino, hydroxy, alkoxy, acylamino, acyloxy, alkyl, halide, and the like, or the monomers may install electron-rich aryl groups in the backbone of the polymer, such that the polymer exhibits fluorescence emission at longer wavelengths. FIG. 11 shows several illustrative embodiments for the synthesis of electron-rich monomers containing amine groups. In some embodiments, the polymer may tailored to advantageously have a large Stokes shift, wherein the fluorescence spectrum is observed at a substantially longer wavelength than the excitation spectrum. In some embodiments, an electron-rich monomer may be co-polymerized with an electron-poor monomer to produce polymers having longer wavelength emission.

In some embodiments, the conjugated polymer or oligomer comprises a sterically bulky monomer that may aid in preserving the optical properties of the polymer or oligomer, even in the solid state. That is, the use of sterically bulky monomers may prevent adjacent or nearby neighboring molecules from interacting with each other through, for example, pi-stacking, to cause a decrease in emission. In some cases, the bulky monomer may comprise a non-planar, bicyclic group that is rigidly attached to the polymer backbone, wherein the bicyclic group comprises bridgehead atoms that are not adjacent to one another. A "rigid" group refers to a group that does not easily rotate about a bond axis, preferably a bond that binds the rigid group to the polymer. In one embodiment, the rigid group rotates no more than about 180°, preferably no more than about 120° and more preferably no more than about 60°. Certain types of rigid groups can provide a polymer with a backbone separated from an adjacent backbone at a distance of at least about 4.5 Å and more preferably at least about 5.0 Å. In one embodiment, the rigid groups are incorporated as pendant groups. Examples of bulky monomers may include monomers comprising surfactants, proteins, or sterically large and/or non-planar organic groups such as pentiptycenes having five arene planes, triptycenes having three arene planes, or other iptycene and iptycene-related moieties. By minimizing the intermolecular pi-pi interactions between nearby or adjacent polymers, the shape of the emission spectra may remain substantially the same as the conjugated polymers are formed into particles or are aggregated in the solid-state.

It is an advantageous feature of the present invention to provide luminescent polymers having a molecular structure that reduces pi-stacking interactions, resulting in increased quantum yields and/or luminescence lifetimes. It is particularly advantageous that these enhanced properties can be achieved when the polymer is provided as a solid state material, e.g. a film. In one embodiment, the film comprising a luminescent polymer has a quantum yield of at least about 0.05 times the quantum yield of the luminescent polymer in solution, more preferably at least about 0.1 times the quantum yield of the luminescent polymer in solution, more preferably at least about 0.15 times the quantum yield of the luminescent polymer in solution, more preferably at least about 0.2 times the quantum yield of the luminescent polymer in solution, more preferably at least about 0.25 times the quantum yield of the luminescent polymer in solution, more preferably at least about 0.3 times the quantum yield of the luminescent polymer in solution, more preferably at least about 0.4 times the quantum yield of the luminescent polymer in solution, and more preferably still about 0.5 times the quantum yield of the luminescent polymer in solution.

The polymer can be a homo-polymer or a co-polymer such as a random co-polymer or a block co-polymer. In one embodiment, the polymer is a block co-polymer. An advantageous feature of block co-polymers is that they may mimic a multi-layer structure, wherein each block may be designed to have different band gap components and, by nature of the chemical structure of a block co-polymer, each band gap component is segregated. As described herein, the band gap and/or selectivity for particular analytes can be achieved by modification or incorporation of different polymer types. The polymer compositions can vary continuously to give a tapered block structure and the polymers can be synthesized by either step growth or chain growth methods.

As used herein, the term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted with additional groups, as described further below. Examples of alkyl groups include, but are not limited to, methyl, ethyl, propyl, isopropyl, cyclopropyl, butyl, isobutyl, tert-butyl, cyclobutyl, hexyl, cyclochexyl, and the like.

The term "heteroalkyl" refers to an alkyl group as described herein in which one or more carbon atoms is replaced by a heteroatom. Suitable heteroatoms include oxygen, sulfur, nitrogen, phosphorus, and the like. Examples of heteroalkyl groups include, but are not limited to, alkoxy, amino, thioester, and the like.

The terms "alkene" and "alkyne" refer to unsaturated aliphatic groups analogous in length and possible substitution to the alkyls described above, but that contain at least one double or triple bond respectively.

The terms "heteroalkene" and "heteroalkyne" refer to unsaturated aliphatic groups analogous in length and possible substitution to the heteroalkyls described above, but that contain at least one double or triple bond respectively.

As used herein, the term "halogen" or "halide" designates —F, —Cl, —Br or —I.

The term "aryl" refers to aromatic carbocyclic groups, optionally substituted, having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl). That is, at least one ring may have a conjugated pi electron system, while other, adjoining rings can be cycloalkyls, cycloalkenyls, cycloalkynyls, aryls and/or heterocyclyls. The aryl group may be optionally substituted, as described herein. "Carbocyclic aryl groups" refer to aryl groups wherein the ring atoms on the aromatic ring are carbon atoms. Carbocyclic aryl groups include monocyclic carbocyclic aryl groups and polycyclic or fused compounds (e.g., two or more adjacent ring atoms are common to two adjoining rings) such as naphthyl groups.

The terms "heteroaryl" refers to aryl groups comprising at least one heteroatom as a ring atom.

As described herein, the term "heterocycle" refers to cyclic groups containing at least one heteroatom as a ring atom, in some cases, 1 to 3 heteroatoms as ring atoms, with the remainder of the ring atoms being carbon atoms. Suitable heteroatoms include oxygen, sulfur, nitrogen, phosphorus, and the like. The term "heterocycle" may include heteroaryl groups, saturated heterocycles (e.g., cycloheteroalkyl) groups, or combinations thereof. The heterocycle may be a saturated molecule, or may comprise one or more double bonds. In some case, the heterocycle is a nitrogen heterocycle, wherein at least one ring comprises at least one nitrogen ring atom. The heterocycles may be fused to other rings to form a polycyclic heterocycle. The heterocycle may also be fused to a spirocyclic group. In some cases, the heterocycle may be attached to a compound via a nitrogen or a carbon atom in the ring.

Heterocycles include, for example, thiophene, benzothiophene, thianthrene, furan, tetrahydrofuran, pyran, isobenzofuran, chromene, xanthene, phenoxathiin, pyrrole, dihydropyrrole, pyrrolidine, imidazole, pyrazole, pyrazine, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, triazole, tetrazole, oxazole, isoxazole, thiazole, isothiazole, phenanthridine, acridine, pyrimidine, phenanthroline, phenazine, phenarsazine, phenothiazine, furazan, phenoxazine, pyrrolidine oxolane, thiolane, oxazole, oxazine, piperidine, homopiperidine (hexamethyleneimine), piperazine (e.g., N-methyl piperazine), morpholine, lactones, lactams such as azetidinones and pyrrolidinones, sultams, sultones, other saturated and/or unsaturated derivatives thereof, and the like. The heterocyclic ring can be optionally substituted at one or more positions with such substituents as described herein. In some cases, the heterocycle may be bonded to a compound via a heteroatom ring atom. In some cases, the heterocycle may be bonded to a compound via a carbon ring atom. In some cases, the heterocycle is pyrrolidine, piperidine, or morpholine.

The term "alkoxy" refers to the group, O-alkyl.

The terms "amine" and "amino" are art-recognized and refer to both unsubstituted and substituted amines, e.g., a moiety that can be represented by the general formula: $N(R')(R'')(R''')$ wherein $R'$, $R''$, and $R'''$ each independently represent a group permitted by the rules of valence.

As used herein, the term "substituted" is contemplated to include all permissible substituents of organic compounds, "permissible" being in the context of the chemical rules of valence known to those of ordinary skill in the art. It will be understood that "substituted" also includes that the substitution results in a stable compound, e.g., which does not spontaneously undergo transformation such as by rearrangement, cyclization, elimination, etc. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" group must still comprise the phenyl moiety and can not be modified by substitution, in this definition, to become, e.g., a pyridine ring. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms.

Examples of substituents include, but are not limited to, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, $-CF_3$, $-CN$, aryl, aryloxy, perhaloalkoxy, aralkoxy, heteroaryl, heteroaryloxy, heteroarylalkyl, heteroaralkoxy, azido, amino, halide, alkylthio, oxo, acylalkyl, carboxy esters, carboxamido, acyloxy, aminoalkyl, alkylaminoaryl, alkylaryl, alkylaminoalkyl, alkoxyaryl, arylamino, aralkylamino, alkylsulfonyl, -carboxamidoalkylaryl, -carboxamidoaryl, hydroxyalkyl, haloalkyl, alkylaminoalkylcarboxy-, aminocarboxamidoalkyl-, cyano, alkoxyalkyl, perhaloalkyl, arylalkyloxyalkyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments; of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one".

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified jay the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements Mother than A), in yet another embodiment, to both A and B (optionally including other elements), etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of", when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Example 1

In order to select optimally sensitive and operationally useful luminescent polymers for the detection of DMNB, polymers were designed to have electronic structures having greater photoreduction abilities. FIG. 2B illustrates qualitative energy level diagrams of the materials used in these experiments. Table 1 lists the Stern-Volmer constants [k(sv)] and quenching rate constants [k(q)] from Stem-Volmer experiments with these luminescent polymers with DMNB as the quencher. The variation in the quenching efficiency of the poly(phenylene ethynylene)s (PPEs, P1-3) revealed that the factors controlling the quenching rate constants are multifaceted. Although the pi-donation of the amines reduces the ground state oxidation potential for P3, it also lowers the band gap and thereby reduces the magnitude of P3's excited-state reduction potential. The higher quenching efficiency of P2, with only one amine per repeat unit, is likely due to a balance between these two effects. All of the PPEs investigated showed very poor quenching rate constants, with even the best quenching rate constant falling an order of magnitude less than the diffusion controlled limit.

TABLE 1

DMNB Stern-Volmer Data

| Polymer | λ(em) | τ(f) | k(sv) ($M^{-1}$) | k(q) ($10^9\ M^{-1}s^{-1}$) |
|---|---|---|---|---|
| P1 | 460 nm | 0.6 ns | ~0 | <1 |
| P2 | 475 nm | 1.8 ns | 3.4 | 1.9 |
| P3 | 580 nm | 3.9 ns | <2 | <1 |
| P4 | 416 nm | 0.5 ns | 9.2 | 18 |
| P5 | 413 nm | 0.6 ns | 9.0 | 15 |
| P6 | 452 nm | 1.9 ns | 13 | 6.9 |
| P7 | 512 nm | 4.2 ns | 22 | 5.2 |

In order to increase the excited-state reduction potential and thereby improve the efficacy of the quenching reaction, larger band gap poly(phenylene)s (PPs, P4-P7) were designed and prepared. Polymers P4-P7 are optically blue-shifted relative to polymers P1-P3, due to a non-planar ground state conformation with decreased conjugation. All the PPs investigated gave quenching rate constants significantly higher than P2, the PPE most efficiently quenched by DMNB, supporting the concept that larger band gaps, and therefore higher energy conduction bands, may produce superior performance relative to analogous PPEs. In fact the most blue-shifted PPs are quenched by DMNB with diffusion controlled pseudo-first order rate constants. As would be expected from simple orbital mixing arguments the aryl amines mainly raise the valence band (HOMO) levels and have a smaller perturbation on the conduction band (LUMO) energies, which lowers the band gaps for both PPEs and PPs. The PPs' wider band gap enables more exergonic electron transfer from the higher energy conduction bands to the DMNB LUMO.

Satisfying the energetic constraints of electron transfer quenching is a necessary, but not a sufficient condition for the trace detection of vapor phase analytes with solid-state AFPs.

The degree of fluorescence quenching of polymers in the solid state by DMNB is also dependent upon other factors, such as the vapor pressure of the analyte, its binding constant to the fluorescent polymer film, and the mobility of excitons within polymers in the solid-state.

Example 2

The ability of luminescent polymers to detect DMNB vapor was studied. Thin films of selected luminescent polymers were simultaneously irradiated and exposed to equilibrium vapor pressures of DMNB. In order to probe the effect of analyte molecular shape, benzophenone was also investigated as a vapor phase quencher. Benzophenone has a reduction potential (−1.6 V vs. SCE) similar to that of DMNB as well as a similar equilibrium vapor pressure ($1.93 \times 10^{-3}$ torr at 25° C.). In contrast to DMNB, the flat structure of benzophenone could allow for strong pi-stacking with the polymer film.

The experiments were carried out on a commercial Fido™ instrument manufactured by Nomadics Inc., which continuously monitors the total fluorescence during vapor sampling.

Upon exposure to DMNB vapor, solid-state fluorescence quenching by the PPEs was observed to be very weak relative to the PPs, with only P2 giving a 4-5% fluorescence attenuation in the presence of DMNB vapor.

Figure 3:
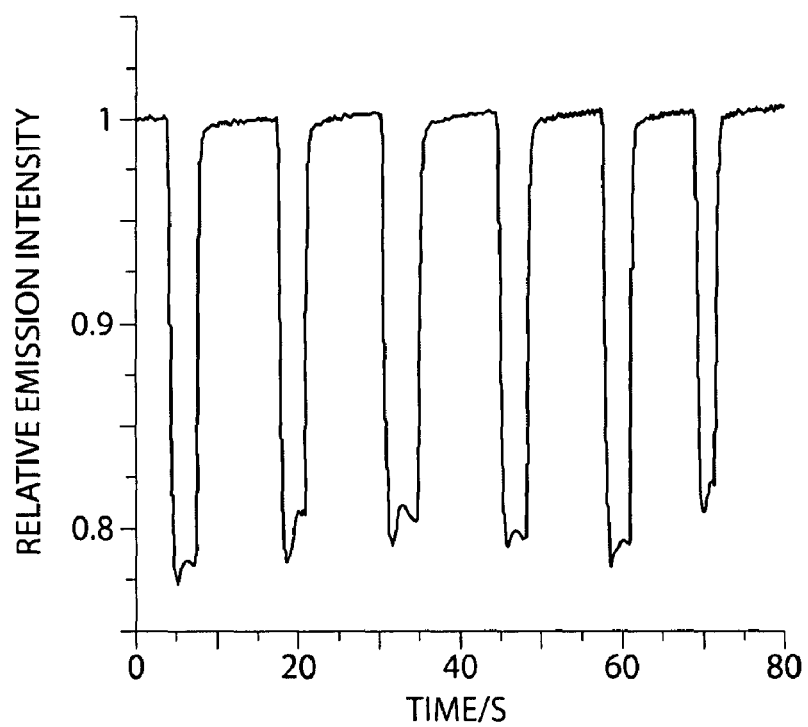
FIG. 3 shows the fluorescence emission intensity response of a thin film of polymer P5 to repeated variable time exposures to equilibrium DMNB vapor.

FIG. 3 shows the fluorescence emission intensity response of a thin film of P5 to repeated variable time exposures to equilibrium DMNB vapor.

Table 2 summarizes the results of the solid-state quenching experiments. The percentage of quenching due to equilibrium benzophenone vapor correlates well with the electron density on the polymer chain, with the diamine-containing P7 showing an average response of 60% quenching under constant flow. These results are consistent with strong polymer-analyte pi-stacking, since polymers with more electron-rich pi systems will have a higher affinity for the more planar benzophenone. The larger binding affinity of benzophenone is also revealed in its temporal response in the sensor. The sensor response in FIG. 3 shows that, at short exposure times, the binding interaction between the polymer and DMNB is highly reversible, indicating a weak binding (rapid off-rate).

Figure 4:
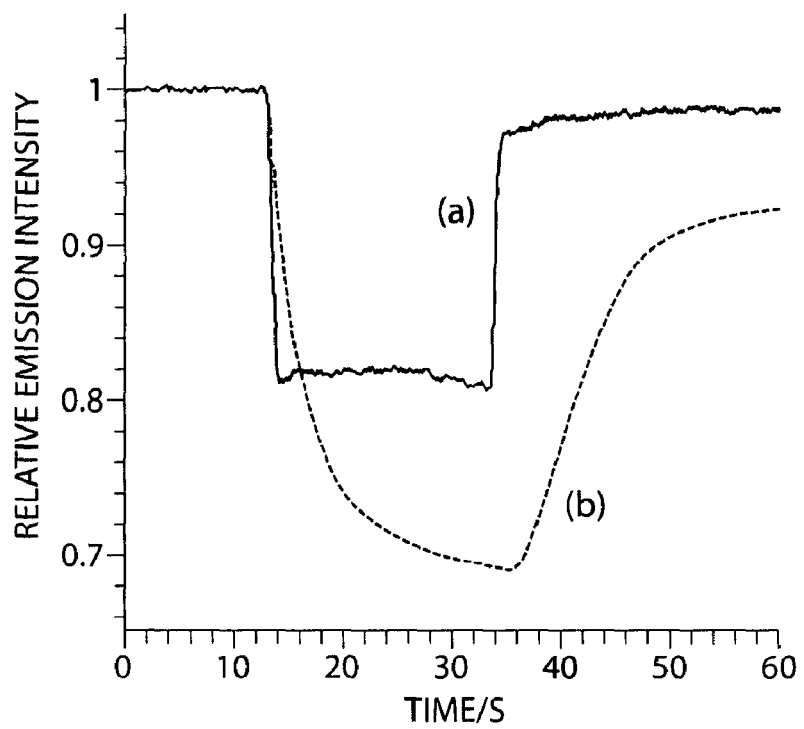
FIG. 4 shows the fluorescence emission intensity response of a thin film of polymer P5 upon a ~20 s exposure to equilibrium vapor of either (a) DMNB or (b) benzophenone.

FIG. 4 shows the fluorescence emission intensity response of a thin film of P5 upon a ~20 s exposure to equilibrium vapor of either (a) DMNB or (b) benzophenone. The 20 second exposures to either benzophenone or DMNB (FIG. 4) are illustrative of the slower recovery times associated with benzophenone that indicate stronger binding constants with the luminescent polymers. The larger binding affinity of benzophenone for the very electron-rich P7 versus P6 or other, less-electron rich polymers is large enough to outweigh any other factors that might make P7 less efficient, such as a smaller driving force for electron transfer or decreased exciton mobility,

TABLE 2

Solid-State Quenching Percentages

| Poly | Benzophenone | DMNB |
|---|---|---|
| P4 | 5 ± 1% | 6 ± 1% |
| P5 | 29 ± 3% | 20 ± 5% |
| P6 | 38 ± 3% | 12 ± 3% |
| P7 | 58 ± 7% | 4 ± 1% |

As shown by the data in Table 2, the moderately electron-rich polymer P5 gave a highly reversible and rapid quenching response of about 20%. More electron-rich and more electron-poor polymers gave smaller responses, which may be indicative of several competing factors contributing to the observed results. For example, electrostatic attraction may be a factor in the solid-state detection of DMNB, since on ah absolute scale it is an electron-deficient compound. However, DMNB generally does not form strong pi-stacking interactions, and its binding differences may not, or may only be slightly, affected by the electron density in the pi-system of the polymers described herein.

Other parameters that can affect a particular material's quenching efficiency in response to an analyte vapor include the rate of PICT, which was demonstrated in the solution experiments to be smaller for the amine-substituted PPs. In addition, the mobility of the excitons in films of P6 and P7 may be substantially smaller than for P5. The large Stokes shift and excited state lifetimes of these materials can be indicative of a substantial structural rearrangement in the excited state. The inability of certain polymer chains to adopt the preferred conformation in the solid-state and the activated nature of conformational changes may impose a "viscous drag" and produce excitons with an higher effective mass.

The efficient detection of very weakly binding analytes may rely on the balance of the parameters described above. In some embodiments, P5 offers a good balance of PICT driving force, electrostatic attraction, and exciton mobility to give a reversible and rapid response to DMNB vapor. In addition, P5, which has previously been investigated for potential use as blue emitter in PLEDs, is highly emissive in the solid state and shows good photochemical stability, especially compared to the amine-containing poly(phenylene)s P6 and P7.

Example 3

Both the solution and solid-state luminescence response of polymers P1b, P2, and P3 to hydrazine vapor was investigated.

UV/vis spectra were recorded on an Agilent 8453 diode-array spectrophotometer and corrected for background signal with a solvent-filled cuvette for solution measurements or a blank cover slip (for solid-state measurements). Emission spectra were acquired on a SPEX Fluorolog-τ3 fluorimeter (model FL-321, 450 W Xenon lamp) using front-face detection for all film samples. Hydrazine hydrate and iodine were purchased from Aldrich and used as received.

The preparation and characterization of polymers investigated in this study has been previously described in Yang, et al., *J. Am. Chem. Soc.* 1998, 120, 12389, Thomas III, et al., *Macromolecules* 2005, 38, 2716, incorporated herein by reference.

For solid-state spectroscopy, thin films were spun-cast onto glass cover slips from an approximately 1 mg/mL chloroform solution at 1500-3000 rpm. Experiments involving equilibrium vapor pressure hydrazine were performed by using a 20-mL size vial that included a piece of cotton and approximately 3 drops of hydrazine hydrate. For spectral responses, this vial was held up to the surface of the film for several seconds. A similar procedure was followed for iodine doping.

Example 4

The temporal responses of the emission signals of films of P1b, P2, and P3 to hydrazine vapor were measured using a FIDO sensing platform manufactured by Nomadics, Inc. The inside of a glass capillary was coated with the conjugated polymer film (spun-cast from a 1 mg/mL solution (THF or $CHCl_3$ at 700 rpm for 1 minute). This capillary was inserted into the sensor, which is equipped with a laser diode. (405 nm) and a photodetector. In addition, a pump, operating at 30-60 cc/min, draws in air from a nozzle through the capillary, exposing the film to an analyte vapor of the users choice (In this work hydrazine or iodine). The total emission is then continuously monitored. Equilibrium concentrations of vapors were introduced by manually holding a vial (20 mL size) that contains some of the analyte solid and a piece of cotton up to the nozzle of the Fido device. Trace concentrations of hydrazine were introduced to the Fido by flowing a known rate of dry nitrogen gas (using a flow meter) through a chamber with controllable temperature. This chamber contained a disposable hydrazine permeation tube (Kin-Tek Laboratories) with a known rate of diffusion. By adjusting the rate of gas flow over the permeation tube, the trace concentration of hydrazine in the gas flow could be accurately changed. Films used for trace hydrazine detection were first irradiated with the Fido light source until they achieved a stable baseline, which typically resulted in an overall weakening of the fluorescence signal. Iodine doping in Fido experiments was achieved by presenting a vial of iodine crystals to the instrument.

Figure 5:
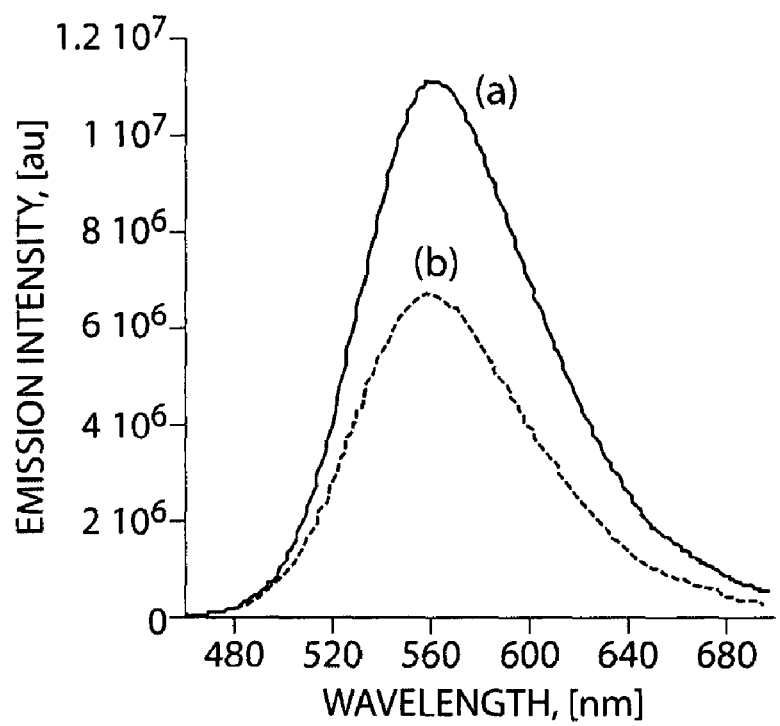
FIG. 5 shows the emission spectra of polymer P3 (a) before and (b) after exposure to a equilibrium vapor of hydrazine for 10 seconds.

FIG. 5 shows the emission spectra of P3 (a) before and (b) after exposure to a equilibrium vapor of hydrazine for 10 seconds. No new emitting species was observed by exposure to hydrazine, since the spectral shape did not change. In addition, the excitation spectrum of the polymer remained the same after the introduction of hydrazine. The other conjugated polymers investigated also showed no change in the shape of their emission spectra upon exposure to hydrazine vapor.

The relative emission enhancements of these polymer films upon exposure to saturated hydrazine vapor was also studied. The aryl diamine-containing polymer P3 gave larger average emission enhancements than the less electron rich P1 or P2 when exposed to saturated hydrazine vapor. Therefore, the most readily oxidized polymer gave the largest emission enhancement. In addition, this enhancement was not observed in solution upon addition of hydrazine. This lack of a solution-phase enhancement may suggest mat mere is a small number of quenching sites within the thin films of the readily oxidized polymers. Exciton and energy migration in conjugated polymers was much more efficient in the solid state than in solution, and the presence of a small number of quenching sites within a thin film can cause a large degree of fluorescence quenching.

These observations, combined with the reducing nature of hydrazine, may suggest that the transduction mechanism for emission enhancement with these materials is an "unquenching" or "turn-on" type of mechanism, in which the addition of hydrazine vapor eliminates a non-radiative decay pathway of the conjugated polymer, resulting in a higher solid-state quantum yield of the conjugated polymer. The non-radiative decay pathway that is suppressed upon addition of hydrazine may be quenching by a small number of oxidized trap sites along the polymer backbone. The removal of these traps by reduction with hydrazine vapor may then lead to a large fluorescence increase, which is larger for materials that are more prone to oxidation under ambient conditions.

Example 5

The effect of hydrazine on the luminescence intensity of the polymers was then studied by first forming photobleached or oxidized films of polymers and exposing them to trace hydrazine vapor. Photooxidation of a film of polymer P2 by simple irradiation in ambient atmosphere at the excitation wavelength for 2-3 min increased the number of oxidized traps along the polymer backbone, as was evidenced by the decrease in fluorescence intensity as a function of irradiation time. This photobleaching procedure allowed for a larger on/off ratio upon exposure to hydrazine vapor. In order to acquire reproducible quantitative data, the polymer films were coated on the inside of a glass capillary and analyzed in a FIDO sensory platform. The FIDO device allowed for the collection of fluorescence intensity data of a thin film while exposed to a continuous flow of analyte vapor. Low concentrations of hydrazine analyte were generated by flowing nitrogen gas past a heated permeation tube with a known rate of hydrazine diffusion. Adjusting the flow rate of $N_2$ allowed for the preparation of a dilute gas-phase sample of hydrazine with a known concentration.

Figure 6:
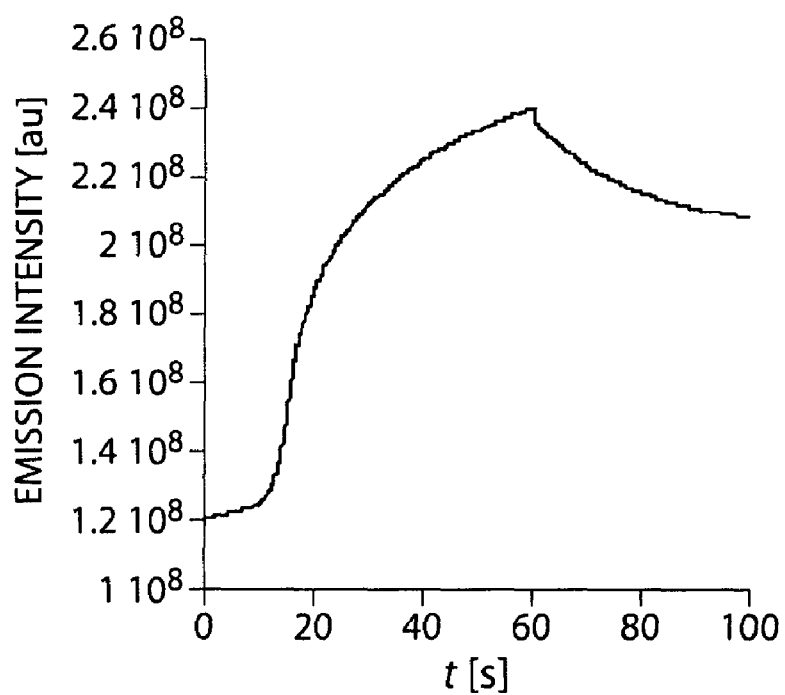
FIG. 6 shows the time-dependent emission of a photobleached film of polymer P2 in a FIDO sensing platform exposed to 1 ppm (permissible exposure limit) hydrazine vapor for 60 seconds.

FIG. 6 shows the time-dependent emission of a photobleached film of P2 in a FIDO sensing platform exposed to 1 ppm (permissible exposure limit) hydrazine vapor for 60 sec. As observed in FIG. 6, the emission intensity increased upon exposure to hydrazine vapor. Such "turn-on" signals have been observed at concentrations as low as 100 parts-per-billion (10% of the permissible exposure limit) hydrazine vapor.

Example 6

Figure 7:
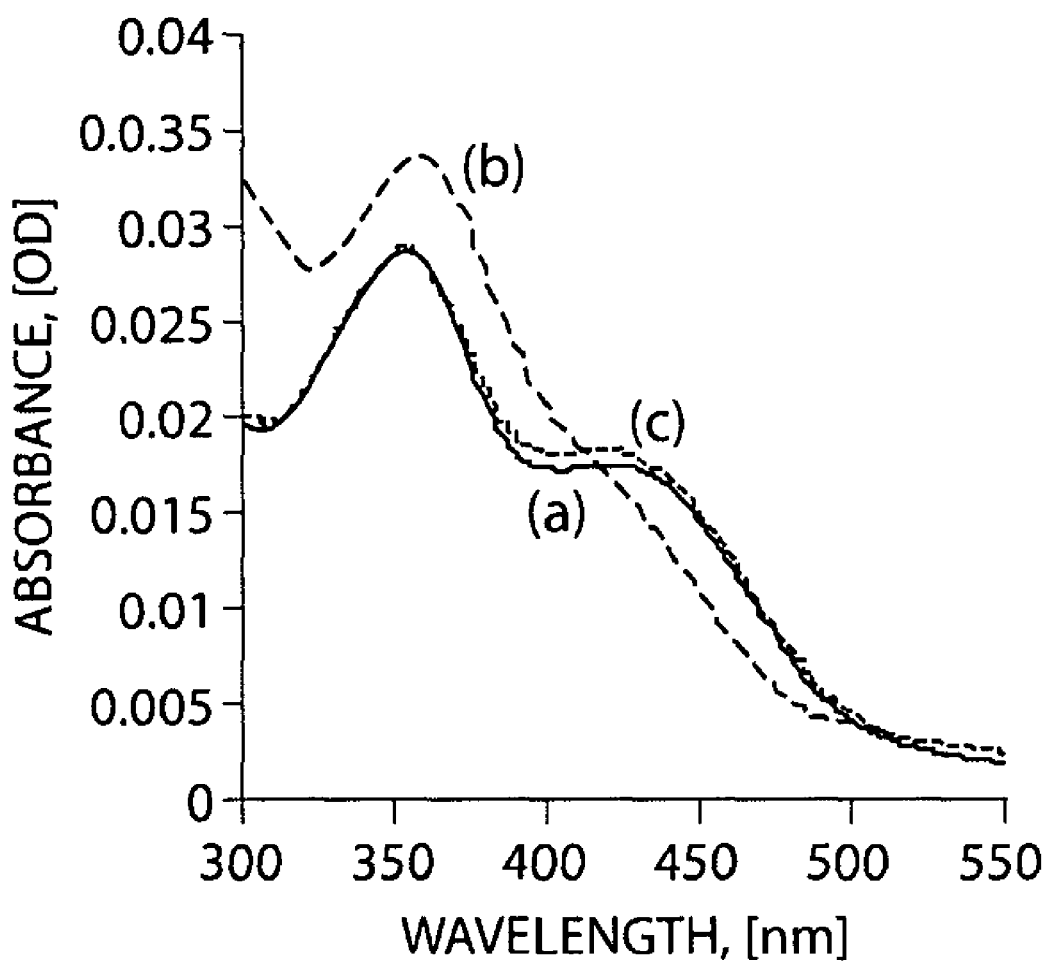
FIG. 7 UV/vis spectra of a film of polymer P3 (a) before exposure to $I_2$ vapor, (b) after exposure to $I_2$ vapor, and (c) after exposure of the $I_2$-doped film to saturated hydrazine vapor for 5 seconds.

The effect of hydrazine on the luminescence intensity of the polymers was also studied by first forming $I_2$-doped films of polymers, wherein molecular iodine was a sacrificial oxidant, to trace hydrazine detection. The k-doped films were then exposed to trace hydrazine vapor as described in Example 5. FIG. 7 shows the UV/vis spectra of a film of P3 (a) before exposure to $I_2$ vapor, (b) after exposure to $I_2$ vapor, and (c) after exposure of the h-doped film to saturated hydrazine vapor for 5 seconds. Exposure to $I_2$ resulted in a significant spectral change of P3, whereas the polymers that are more difficult to oxidize (P1 and P2) showed no evidence of chemical reaction with $I_2$.

Figure 8:
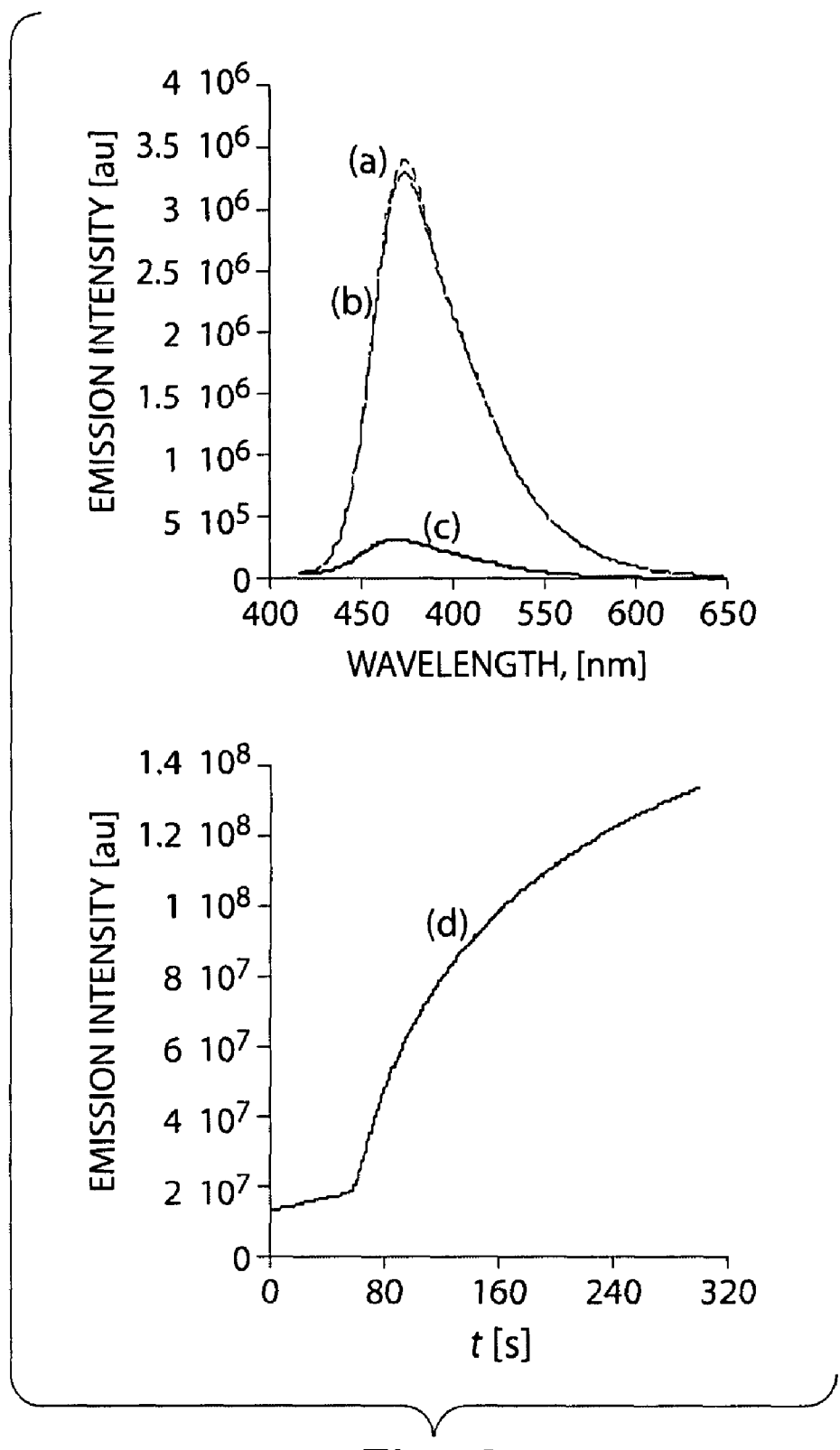
FIG. 8 shows the emission response of polymer P2 (a) before exposure to $I_2$, (c) after exposure to $I_2$ for approximately 5 seconds, and (b) after exposure of the $I_2$-doped film to hydrazine vapor, and (d) the fluorescence trace of the h-doped film exposed to 1 ppm hydrazine.

The intentional inclusion of traps by $I_2$ doping gave a system with a much lower background signal while maintaining the amplified nature of the transduction. Polymers P1-P3 all showed almost complete fluorescence quenching upon exposure to saturated $I_2$ vapor. The observed fluorescence quenching of P1 and P2 by $I_2$ vapor was likely due to intercalation of $I_2$ rather than chemical oxidation. FIG. 8 shows the emission response of polymer P2 (a) before exposure to $I_2$, (c) after exposure to $I_2$ for approximately 5 seconds, and (b) after exposure of the $I_2$-doped film to hydrazine vapor, and (d) the fluorescence trace of the h-doped film exposed to 1 ppm hydrazine. The on/off ratio of this sensory material was much larger than with the pure (e.g., non-$I_2$-doped) polymer, since the intercalated iodine had almost completely quenched the emission of the film. In this example there was a fluorescence enhancement of almost one order of magnitude within five minutes.

As shown in FIG. 8, exposure of the oxidized P2 to saturated hydrazine vapor resulted in a nearly full recovery of solid-state emission with identical spectral shape by reduction of oxidized polymer chains and intercalated iodine. FIG. 9 shows a plot of normalized emission intensity of a film of P3 as a function of time upon exposure to saturated iodine vapor (quench) followed by saturated hydrazine vapor (recovery), illustrating the reproducibility of the process over multiple iodine/hydrazine exposure cycles.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using ho more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present mother cases. Other elements may optionally be present other than the elements specifically identified by the "and/or" clause, whether related or unrelated to those elements specifically identified unless clearly indicated to the contrary. Thus, as a non-limiting example, a reference to "A and/or B", when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number of list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of" when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A, or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed:

1. A method for determination of hydrazine or a hydrazine derivative, comprising:
   providing a material comprising a luminescent polymer, wherein the luminescent polymer comprises at least one oxidized site and/or wherein the luminescent polymer is in contact with at least one quencher molecule;
   exposing the material to a sample suspected of containing hydrazine or a hydrazine derivative, wherein hydrazine and/or the hydrazine derivative, if present, interacts with the luminescent polymer via a redox reaction to cause an increase in the luminescence intensity of the polymer;
   determining the increase in luminescence intensity of the polymer, thereby determining hydrazine or the hydrazine derivative.

2. A method as in claim 1, wherein, in the absence of hydrazine or the hydrazine derivative, the luminescent polymer comprises non-radiative pathways, and, in the presence of hydrazine or the hydrazine derivative, hydrazine or the hydrazine derivative interacts with the luminescent polymer to reduce the number of non-radiative pathways, thereby increasing the luminescence intensity of the polymer.

3. A method as in claim 1, wherein the increase in luminescence intensity further comprises a change in the wavelength of the luminescence.

4. A method as in claim 1, wherein the luminescent polymer is a poly(arylene), poly(arylenevinylene), poly(aryleneethylnylene), and substituted derivatives thereof.

5. A method as in claim 1, wherein the luminescent polymer is poly(aryleneethylnylene).

6. A method as in claim 1, wherein the luminescent polymer has the structure,

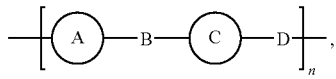

wherein n is at least 1, A and C are optionally substituted aromatic groups, and B and D are alkene, alkyne, heteroalkene, or heteroalkyne.

7. A method as in claim 1, wherein the luminescent polymer has the structure,

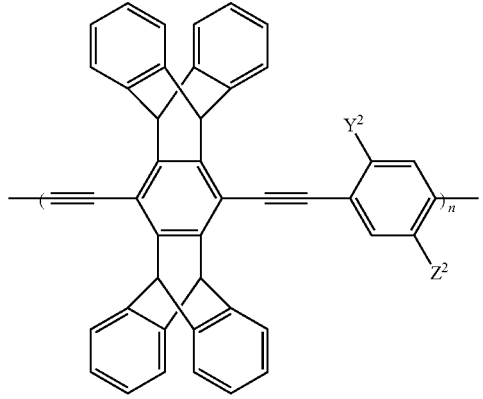

wherein $Y^2$ and $Z^2$ are independently alkyl, alkoxy, amino, and substituted derivatives thereof.

8. A method as in claim 7, wherein $Y^2$ and $Z^2$ are alkoxy.

9. A method as in claim 7, wherein $Y^2$ and $Z^2$ are $NR^1R^2$, wherein $R^1$ and $R^2$ are alkyl.

10. A method as in claim 7, wherein $Y^2$ is hydrogen and $Z^2$ is $NR^1R^2$, wherein $R^1$ and $R^2$ are alkyl.

11. A method as in claim 7, wherein the luminescent polymer has the structure,

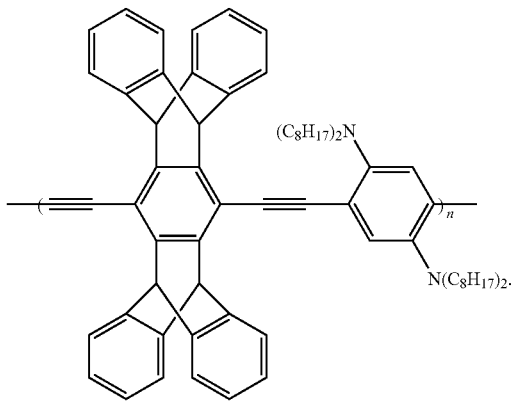

12. A method as in claim 7, wherein the luminescent polymer has the structure,

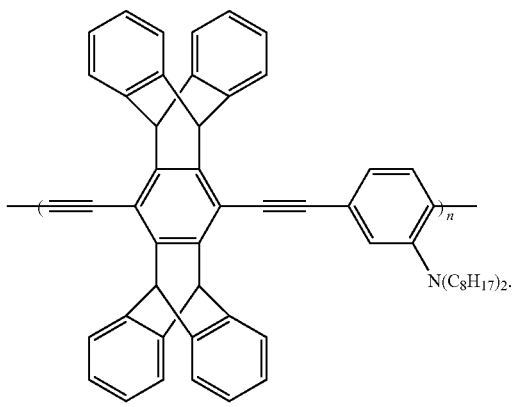

13. A method as in claim 1, wherein the luminescent polymer comprises a heterocycle, optionally substituted.

14. A method as in claim 1, wherein the luminescent polymer comprises a triazole group, optionally substituted.

15. A method as in claim 1, wherein the luminescent polymer comprises a pendant group comprising a triazole group, optionally substituted.

16. A method as in claim 1, wherein the luminescent polymer has the structure,

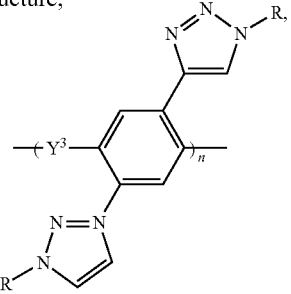

wherein
  $Y^3$ is alkene, alkyne, aryl, heteroalkene, heteroalkyne, or heteroaryl, optionally substituted; and
  R is aryl or alkyl, optionally substituted; and
  and n is greater than 1.

17. A method as in claim 1, wherein the luminescent polymer comprises oxidized sites and the hydrazine or hydrazine derivative reduces the oxidized sites.

18. A method as in claim 1, wherein the luminescent polymer comprises a quenching molecule associated with the luminescent polymer and the hydrazine or hydrazine derivative reduces the quenching molecule.

19. A method as in claim 18, wherein the quenching molecule is $I_2$.

20. A method as in claim 1, wherein, in the presence of hydrazine or the hydrazine derivative, the luminescence intensity of the polymer increases by at least 25% relative to the luminescence intensity of the polymer in the absence of hydrazine or the hydrazine derivative upon exposure to the same conditions of electromagnetic radiation.

21. A method as in claim 1, wherein, in the presence of hydrazine or the hydrazine derivative, the luminescence intensity of the polymer increases by at least 50% relative to the luminescence intensity of the polymer in the absence of hydrazine or the hydrazine derivative upon exposure to the same conditions of electromagnetic radiation.

22. A method as in claim 1, wherein, in the presence of hydrazine or the hydrazine derivative, the luminescence intensity of the polymer increases by at least 75% relative to the luminescence intensity of the polymer in the absence of hydrazine or the hydrazine derivative upon exposure to the same conditions of electromagnetic radiation.

23. A method as in claim 1, wherein, in the presence of hydrazine or the hydrazine derivative, the luminescence intensity of the polymer increases by at least 100% relative to the luminescence intensity of the polymer in the absence of hydrazine or the hydrazine derivative upon exposure to the same conditions of electromagnetic radiation.

24. A method as in claim 1, wherein, in the presence of hydrazine or the hydrazine derivative, the luminescence intensity of the polymer increases by at least 250% relative to the luminescence intensity of the polymer in the absence of hydrazine or the hydrazine derivative upon exposure to the same conditions of electromagnetic radiation.

25. A method as in claim 1, wherein, in the presence of hydrazine or the hydrazine derivative, the luminescence intensity of the polymer increases by at least 500% relative to the luminescence intensity of the polymer in the absence of hydrazine or the hydrazine derivative upon exposure to the same conditions of electromagnetic radiation.

26. A method as in claim 1, wherein, in the presence of hydrazine or the hydrazine derivative, the luminescence intensity of the polymer increases by at least 750% relative to the luminescence intensity of the polymer in the absence of hydrazine or the hydrazine derivative upon exposure to the same conditions of electromagnetic radiation.

27. A method as in claim 1, wherein, in the presence of hydrazine or the hydrazine derivative, the luminescence intensity of the polymer increases by at least 1000% relative to the luminescence intensity of the polymer in the absence of hydrazine or the hydrazine derivative upon exposure to the same conditions of electromagnetic radiation.

28. A method as in claim 1, wherein hydrazine or the hydrazine derivative, when present, is present in trace quantities.

29. A method for determining an analyte by increasing the luminescence intensity of a polymer, comprising:
exposing a material comprising a luminescent polymer to an analyte comprising hydrazine or a hydrazine derivative,
wherein, in the absence of the analyte, the luminescent polymer comprises non-radiative pathways, and, in the presence of the analyte, the analyte interacts with the material via a redox reaction to reduce the number of non-radiative pathways of the polymer, thereby increasing the luminescence intensity of the polymer.

30. A method as in claim 29, wherein the increase in luminescence intensity further comprises a change in the wavelength of the luminescence.

31. A method as in claim 29, wherein the luminescent polymer comprises oxidized sites and the hydrazine or hydrazine derivative reduces the oxidized sites.

32. A method as in claim 29, wherein the luminescent polymer comprises a quenching molecule associated with the luminescent polymer and the hydrazine or hydrazine derivative reduces the quenching molecule.

33. A method as in claim 32, wherein the quenching molecule is $I_2$.

34. A method as in claim 29, wherein, in the presence of hydrazine or the hydrazine derivative, the luminescence intensity of the polymer increases by at least 25% relative to the luminescence intensity of the polymer in the absence of hydrazine or the hydrazine derivative upon exposure to the same conditions of electromagnetic radiation.

35. A method as in claim 29, wherein, in the presence of hydrazine or the hydrazine derivative, the luminescence intensity of the polymer increases by at least 50% relative to the luminescence intensity of the polymer in the absence of hydrazine or the hydrazine derivative upon exposure to the same conditions of electromagnetic radiation.

36. A method as in claim 29, wherein, in the presence of hydrazine or the hydrazine derivative, the luminescence intensity of the polymer increases by at least 75% relative to the luminescence intensity of the polymer in the absence of hydrazine or the hydrazine derivative upon exposure to the same conditions of electromagnetic radiation.

37. A method as in claim 29, wherein, in the presence of hydrazine or the hydrazine derivative, the luminescence intensity of the polymer increases by at least 100% relative to the luminescence intensity of the polymer in the absence of hydrazine or the hydrazine derivative upon exposure to the same conditions of electromagnetic radiation.

38. A method as in claim 29, wherein, in the presence of hydrazine or the hydrazine derivative, the luminescence intensity of the polymer increases by at least 250% relative to the luminescence intensity of the polymer in the absence of hydrazine or the hydrazine derivative upon exposure to the same conditions of electromagnetic radiation.

39. A method as in claim 29, wherein, in the presence of hydrazine or the hydrazine derivative, the luminescence intensity of the polymer increases by at least 500% relative to the luminescence intensity of the polymer in the absence of hydrazine or the hydrazine derivative upon exposure to the same conditions of electromagnetic radiation.

40. A method as in claim 29, wherein, in the presence of hydrazine or the hydrazine derivative, the luminescence intensity of the polymer increases by at least 750% relative to the luminescence intensity of the polymer in the absence of hydrazine or the hydrazine derivative upon exposure to the same conditions of electromagnetic radiation.

41. A method as in claim 29, wherein, in the presence of hydrazine or the hydrazine derivative, the luminescence intensity of the polymer increases by at least 1000% relative to the luminescence intensity of the polymer in the absence of hydrazine or the hydrazine derivative upon exposure to the same conditions of electromagnetic radiation.

* * * * *